United States Patent
Klatzmann et al.

(10) Patent No.: US 11,559,566 B2
(45) Date of Patent: *Jan. 24, 2023

(54) USE OF LOW DOSE IL-2 FOR TREATING AUTOIMMUNE-RELATED OR INFLAMMATORY DISORDERS

(71) Applicants: INSERM (Institut National de la Sante et de la Recherche Medicale), Paris (FR); ASSISTANCE PUBLIQUE HOPITAUX DE PARIS, Paris (FR); SORBONNE UNIVERSITE, Paris (FR)

(72) Inventors: David Klatzmann, Paris (FR); David Saadoun, Neuilly sur Seine (FR); Patrice Cacoub, Le Perreux (FR); Michèle Rosenzwajg, Paris (FR); Eliane Piaggio, Paris (FR); Gilbert Bensimon, Villejuif (FR); Claude Bernard, Malakoff (FR)

(73) Assignees: INSERM (Institut National de la Sante et de la Recherche Medicale), Paris (FR); ASSISTANCE PUBLIQUE HOPITAUX DE PARIS, Paris (FR); SORBONNE UNIVERSITE, Paris (FR)

( * ) Notice: Subject to any disclaimer, the term of this patent is extended or adjusted under 35 U.S.C. 154(b) by 284 days.

This patent is subject to a terminal disclaimer.

(21) Appl. No.: 16/925,983

(22) Filed: Jul. 10, 2020

(65) Prior Publication Data
US 2021/0038691 A1 Feb. 11, 2021

Related U.S. Application Data

(63) Continuation of application No. 16/361,902, filed on Mar. 22, 2019, now Pat. No. 10,765,723, which is a continuation of application No. 15/588,226, filed on May 5, 2017, now Pat. No. 10,293,028, which is a continuation of application No. 14/004,211, filed as application No. PCT/EP2012/054174 on Mar. 9, 2012, now Pat. No. 9,669,071.

(60) Provisional application No. 61/451,663, filed on Mar. 11, 2011.

(30) Foreign Application Priority Data

Mar. 11, 2011 (EP) .................................. 1305269

(51) Int. Cl.
A61K 38/20 (2006.01)

(52) U.S. Cl.
CPC ............................ *A61K 38/2013* (2013.01)

(58) Field of Classification Search
CPC ................................................. A61K 38/2013
See application file for complete search history.

(56) References Cited

U.S. PATENT DOCUMENTS

| 5,466,447 A | 11/1995 | Abels et al. |
| 9,669,071 B2 | 6/2017 | Klatzmann et al. |
| 10,293,028 B2 | 5/2019 | Klatzmann et al. |
| 10,765,723 B2 | 9/2020 | Klatzmann et al. |
| 2011/0150826 A1 | 6/2011 | Paulsen et al. |

FOREIGN PATENT DOCUMENTS

| EP | 0262802 A2 | 6/1988 |
| WO | WO 91/14444 A1 | 10/1991 |
| WO | WO 99/18992 A1 | 4/1999 |
| WO | WO 99/26660 A2 | 6/1999 |
| WO | WO 02/078624 A2 | 10/2002 |
| WO | WO 2005/007121 A2 | 1/2005 |
| WO | WO 2007/084651 A2 | 7/2007 |
| WO | WO 2009//112502 A1 | 9/2009 |
| WO | WO 2010/049438 A2 | 5/2010 |
| WO | WO 2010/085495 A1 | 7/2010 |
| WO | WO 2012/065212 A1 | 5/2012 |

OTHER PUBLICATIONS

[No Author Listed], Declaration by Pr. David Klatzmann for EP Application No. 12708029.9, foreign counterpart of U.S. Appl. No. 16/361,902, dated Jun. 11, 2017. 7 pages.
[No Author Listed], Second Declaration by Pr. David Klatzmann for EP Application No. 12708029.9, foreign counterpart of U.S. Appl. No. 16/361,902, dated Aug. 17, 2020. 6 pages.
[No Author Listed], Third Declaration by Pr. David Klatzmann for EP Application No. 12708029.9, foreign counterpart of U.S. Appl. No. 16/361,902, dated Jan. 20, 2021. 2 pages.
[No Author Listed], Declaration by Pr. David Klatzmann for EP Application No. 18179669.9, foreign counterpart of U.S. Appl. No. 16/361,902, dated Jun. 26, 2019. 7 pages.
[No Author Listed], Notice of Opposition for EP Application No. 12708029.9, foreign counterpart of U.S. Appl. No. 16/361,902, dated Apr. 30, 2019. 32 pages.
[No Author Listed], Third Party Observations on EP Application No. 12708029.9, foreign counterpart of U.S. Appl. No. 16/361,902, dated Oct. 19, 2016. 8 pages.
[No Author Listed], CTLL-2 (ATCC® TIB-214™)—Characteristics. ATCC. Jul. 28, 2020. 1 page. Accessible at atcc.org/Products/All/TIB-214.aspx#characteristics.
[No Author Listed], Guidance for Industry: Estimating the Maximum Safe Starting Dose in Initial Clinical Trials for Therapeutics in Adult Healthy Volunteers. U.S. Department of Health and Human Service, Food and Drug Administration, Center for Drug Evaluation and Research. Jul. 2005. 30 pages.
[No Author Listed], HT-2 clone A5E (ATCC ®CRL-1841™)—Characteristics. ATCC. Jul. 28, 2020, 1 page. Accessible at atcc.org/products/all/CRL-1841.aspx#characteristics.
[No Author Listed], WHO International Standard: 1$^{st}$ Standard for Interleukin 2 (Human, Jurkat derived). NIBSC code: 86/504, version 6.0. May 28, 2014; 2 pages.

(Continued)

*Primary Examiner* — Prema M Mertz
(74) *Attorney, Agent, or Firm* — McDermott Will & Emery LLP

(57) ABSTRACT

The present invention relates to novel therapies for treating autoimmune and inflammatory diseases. More specifically, the present invention relates to a use of low dose interleukin-2 for the treatment of type I diabetes and other autoimmune and/or inflammatory diseases.

16 Claims, 11 Drawing Sheets

(56) References Cited

OTHER PUBLICATIONS

Figure 1:
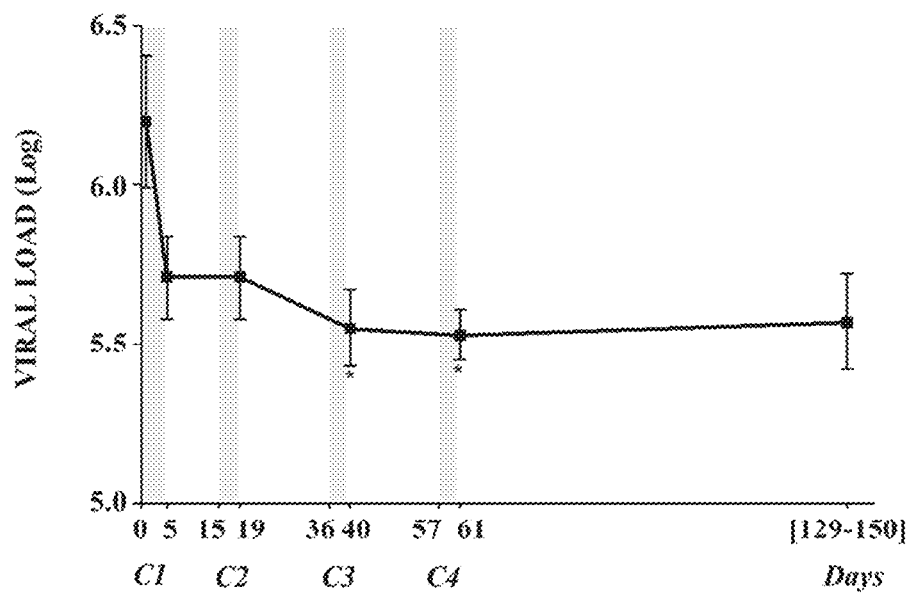
Figure 1:
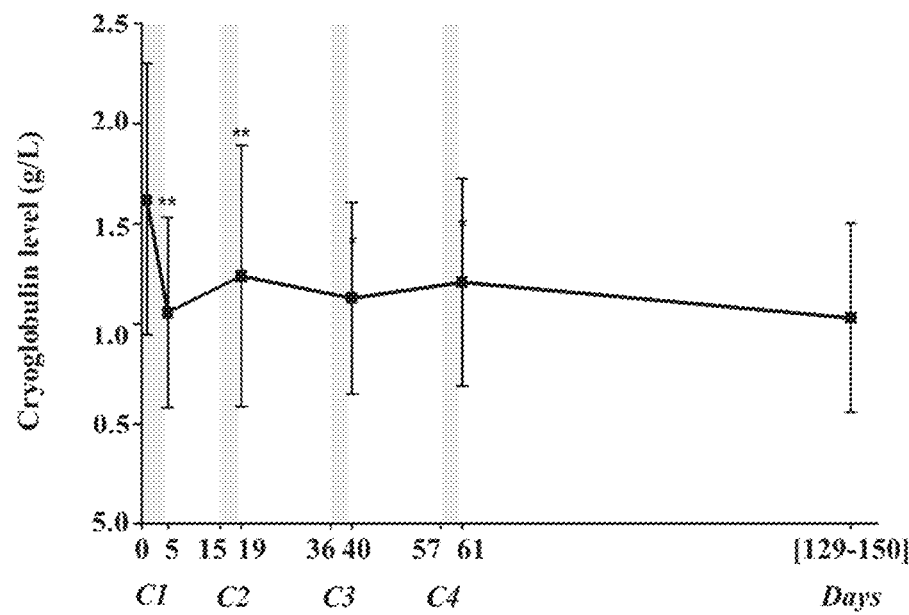
Figure 1:
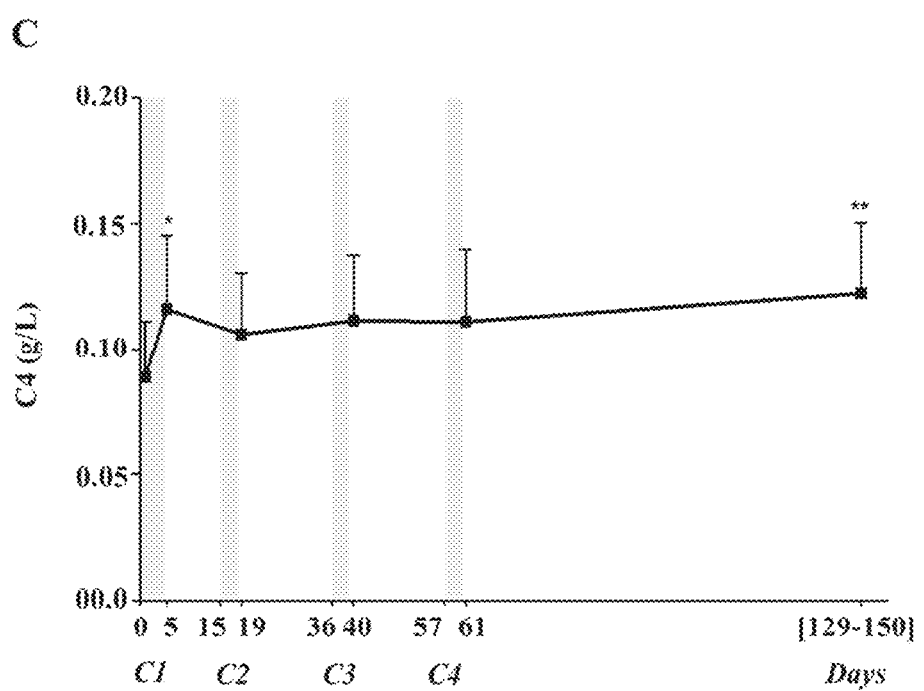

[No Author Listed], WHO International Standard: 2$^{nd}$ International Standard for Interleukin 2 (Human, rDNA derived). NIBSC code: 86/500, version 1.0. Apr. 23, 2013; 2 pages.

Bluestone, The yin and yang of interleukin-2-mediated immunotherapy. N Engl J Med. Dec. 1, 2011;365(22):2129-31.

Bluestone et al., Type 1 diabetes immunotherapy using polyclonal regulatory T cells. Sci Transl Med. Nov. 25, 2015;7(315):315ra189(1-15).

D'Hennezel et al., IL-2 as a therapeutic target for the restoration of Foxp3+ regulatory T cell function in organ-specific autoimmunity: implications in pathophysiology and translation to human disease. J Transl Med. Nov. 8, 2010;8:113(1-12).

Dendrou et al., Cell-specific protein phenotypes for the autoimmune locus IL2RA using a genotype-selectable human bioresource. Nat Genet. Sep. 2009;41(9):1011-5, Epub Aug. 23, 2009.

Garg et al., Type 1 diabetes-associated IL2RA variation lowers IL-2 signaling and contributes to diminished CD4+CD25+ regulatory T cell function. J Immunol. May 1, 2012;188(9):4644-53. Epub Mar. 28, 2012.

Greenbaum, History of Changes for Study: Proleukin and Rapamune in Type 1 Diabetes. Identifier NCT00525889. clinicaltrials.gov/ct2/show/NCT00525889. Published Feb. 6, 2017. 7 pages.

Grinberg-Bleyer et al., IL-2 reverses established type 1 diabetes in NOD mice by a local effect on pancreatic regulatory T cells. J Exp Med. Aug. 30, 2010;207(9):1871-8. Epub Aug. 2, 2010.

Hank et al., Distinct clinical and laboratory activity of two recombinant interleukin-2 preparations. Clin Cancer Res. Feb. 1999;5(2):281-9.

Hartemann et al., Low-dose interleukin 2 in patients with type 1 diabetes: a phase 1/2 randomised, double-blind, placebo-controlled trial. Lancet Diabetes Endocrinol. Dec. 2013;1(4):295-305. Epub Oct. 8, 2013.

Hori et al., Establishment of an interleukin 2-dependent human T cell line from a patient with T cell chronic lymphocytic leukemia who is not infected with human T cell leukemia/lymphoma virus. Blood. Oct. 1987;70(4):1069-72.

Hulme et al., Central role for interleukin-2 in type 1 diabetes. Diabetes. Jan. 2012;61(1):14-22.

Humrich et al., Homeostatic imbalance of regulatory and effector T cells due to IL-2 deprivation amplifies murine lupus. Proc Natl Acad Sci USA, Jan. 5, 2010;107(1):204-9. Epub Dec. 14, 2009.

Klatzmann, Dose-effect Relationship of Low-dose IL-2 in Type 1 Diabetes (DF-IL2). Identifier NCT01353833. clinicaltrials.gov/ct2/show/NCT01353833. Published May 16, 2011. 8 pages.

Klatzmann et al., The promise of low-dose interleukin-2 therapy for autoimmune and inflammatory diseases. Nat Rev Immunol. May 2015;15(5):283-94. Epub Apr. 17, 2015.

Klein et al., Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology. Jan. 11, 2017;6(3):e1277306(1-17).

Koreth et al., Interleukin-2 and regulatory T cells in graft-versus-host disease. N Engl J Med. Dec. 1, 2011;365(22):2055-66.

Long et al., Defects in IL-2R signaling contribute to diminished maintenance of FOXP3 expression in CD4(+)CD25(+) regulatory T-cells of type 1 diabetic subjects. Diabetes. Feb. 2010;59(2):407-15. Epub Oct. 29, 2009.

Long et al., Rapamycin/IL-2 combination therapy in patients with type 1 diabetes augments Tregs yet transiently impairs β-cell function. Diabetes. Sep. 2012;61(9):2340-8. Epub Jun. 20, 2012.

Lu, Practical Clinical Drug Handbook, 2$^{nd}$ Ed. Phoenix Science Press. Jan. 2002. 249 pages.

Lyons et al., Congenic mapping of the type 1 diabetes locus, Idd3, to a 780-kb region of mouse chromosome 3: identification of a candidate segment of ancestral DNA by haplotype mapping. Genome Res. Apr. 2000;10(4):446-53.

Rabinovitch et al., Combination therapy with sirolimus and interleukin-2 prevents spontaneous and recurrent autoimmune diabetes in NOD mice. Diabetes. Mar. 2002;51(3):638-45.

Rosenzwajg et al., Low-dose interleukin-2 fosters a dose-dependent regulatory T cell tuned milieu in TID patients. J Autoimmun. Apr. 2015;58:48-58. Epub Jan. 26, 2015.

Saadoun et al., Regulatory T-cell responses to low-dose interleukin-2 in HCV-induced vasculitis. N Engl J Med. Dec. 1, 2011;365(22):2067-77. Erratum in: N Engl J Med. Feb. 20, 2014;370(8):786.

Sakaguchi et al., Immunologic self-tolerance maintained by activated T cells expressing IL-2 receptor alpha-chains (CD25). Breakdown of a single mechanism of self-tolerance causes various autoimmune diseases. J Immunol. Aug. 1, 1995;155(3):1151-64.

Shanafelt et al., A T-cell-selective interleukin 2 mutein exhibits potent antitumor activity and is well tolerated in vivo. Nat Biotechnol. Nov. 2000;18(11):1197-202.

Tang et al., Central role of defective interleukin-2 production in the triggering of islet autoimmune destruction. Immunity. May 2008;28(5):687-97. Epub May 8, 2008.

Valencia et al., Deficient CD4+CD25high T regulatory cell function in patients with active systemic lupus erythematosus. J Immunol. Feb. 15, 2007;178(4):2579-88.

Velilla et al., Effect of low-dose IL-2 immunotherapy on frequency and phenotype of regulatory T cells and NK cells in HIV/HCV-coinfected patients. AIDS Res Hum Retrovimses. Jan. 2008;24(1):52-61.

Vella et al., Localization of a type 1 diabetes locus in the IL2RA/CD25 region by use of tag single-nucleotide polymorphisms. Am J Hum Genet. May 2005;76(5):773-9. Epub Mar. 17, 2005.

Velthuis et al., Simultaneous detection of circulating autoreactive CD8+ T-cells specific for different islet cell-associated epitopes using combinatorial MHC multimers. Diabetes. Jul. 2010;59(7):1721-30. Epub Mar. 31, 2010.

Wadhwa et al., Report on a collaborative study for proposed 2$^{nd}$ International Standard for Interleukin-2 (IL-2). World Health Organization. Geneva. Oct. 15-19, 2012. 31 pages.

Wang et al., An association between immunosenescence and CD4(+)CD25(+) regulatory T cells: a systematic review. Biomed Environ Sci. Aug. 2010;23(4):327-32.

Yamanouchi et al., Interleukin-2 gene variation impairs regulatory T cell function and causes autoimmunity. Nat Genet. Mar. 2007;39(3):329-37. Epub Feb. 4, 2007.

Yang et al., Natural Variation in Interleukin-2 Sensitivity Influences Regulatory T-Cell Frequency and Function in Individuals With Long-standing Type 1 Diabetes. Diabetes. Nov. 2015;64(11):3891-902. Epub Jul. 29, 2015.

Yu et al., Selective IL-2 responsiveness of regulatory T cells through multiple intrinsic mechanisms supports the use of low-dose IL-2 therapy in type 1 diabetes. Diabetes. Jun. 2015;64(6):2172-83. Epub Jan. 9, 2015.

[No Author Listed], Proleukin Package Insert—Reference ID 3165255. Prometheus Laboratories Inc. Jul. 2012. 19 pages.

Bombardier et al., Derivation of the SLEDAI. A disease activity index for lupus patients. The Committee on Prognosis Studies in SLE. Arthritis Rheum. Jun. 1992;35(6):630-40.

Boyman et al., Potential use of IL-2/anti-IL-2 antibody immune complexes for the treatment of cancer and autoimmune disease. Expert Opin Biol Ther. Dec. 2006;6(12):1323-31.

Crispin et al., Quantification of regulatory T cells in patients with systemic lupus erythematosus. J Autoimmun. Nov. 2003;21(3):273-6.

Griffiths et a., Assessment of patients with systemic lupus erythematosus and the use of lupus disease activity indices. Best Pract Res Clin Rheumatol. Oct. 2005;19(5):685-708.

He et al., Low-dose interleukin-2 treatment selectively modulates CD4(+) T cell subsets in patients with systemic lupus erythematosus. Nat Med. Sep. 2016;22(9):991-3.

Humrich et al., Rapid induction of clinical remission by low-dose interleukin-2 in a patient with refractoiy SLE. Ann Rheum Dis. Apr. 2015;74(4):791-2. Epub Jan. 21, 2015.

Lee et al., Inverse correlation between CD4+ regulatory T-cell population and autoantibody levels in paediatric patients with systemic lupus erythematosus. Immunology, Feb. 2006;117(2):280-6.

(56) References Cited

OTHER PUBLICATIONS

Malek et al., CD4 regulatory T cells prevent lethal autoimmunity in IL-2Rbeta-deficient mice. Implications for the nomedundant function of IL-2. Immunity. Aug. 2002;17(2):167-78.

Miyara et al., Global natural regulatory T cell depletion in active systemic lupus erythematosus. J Immunol. Dec. 15, 2005;175(12):8392-400.

Miyasaka et al., Interleukin 2 deficiencies in rheumatoid arthritis and systemic lupus eiythematosus. Clin Immunol Immunopatho. Apr. 1984;31(1):109-17.

Petri et al., Classification and definition of major flares in SLE clinical trials. Lupus. 1999;8(8):685-91.

Petri, Review of classification criteria for systemic lupus erythematosus. Rheum Dis Clin North Am. May 2005;31(2):245-54, vi.

Talal et al., Interleukins in Experimental Autoimmune Disease. In: Klein T., Specter S., Friedman H., Szentivanyi A. (eds) Biological Response Modifiers in Human Oncology and Immunology. Advances in Experimental Medicine and Biology, vol. 166, Springer, Boston, MA, 1983. 11 pages.

Tsokos, Systemic lupus erythematosus. N Engl J Med. Dec. 1, 2011;365(22):2110-21.

[No Author Listed], Clinical Trial NCT00525889 "Proleukin and Rapamune in Type 1 Diabetes". U.S. National Library of Medicine. ClinicalTrials.gov archive. Dec. 20, 2010. 7 pages.

Boyer et al., CD4+CD25+ regulatory T-cell deficiency in patients with hepatitis C-mixed cryoglobulinemia vasculitis. Blood. May 1, 2004;103(9):3428-30. Epub Dec. 18, 2003.

Davis et al., Prevalence of detectable C-Peptide according to age at diagnosis and duration of type 1 diabetes. Diabetes Care. Mar. 2015;38(3):476-81. Epub Dec. 17, 2014.

Dufort et al., Cell type-specific immune phenotypes predict loss of insulin secretion in new-onset type 1 diabetes. JCI Insight. Feb. 21, 20191;4(4):e125556(1-16).

Hampe, B Cell in Autoimmune Diseases. Scientifica (Cairo). 2012;2012:215308(1-18).

Kitas et al., Deficient interleukin 2 production in rheumatoid arthritis: association with active disease and systemic complications. Clin Exp Immunol. Aug. 1988;73(2):242-9.

Kuhtreiber et al., Low levels of C-peptide have clinical significance for established Type 1 diabetes. Diabet Med. Oct. 2015;32(10):1346-53. Epub Aug. 16, 2015.

Lieberman et al., The IL-2 defect in systemic lupus erythematosus disease has an expansive effect on host immunity. J Biomed Biotechnol. 2010;2010:740619(1-6). Epub Jun. 6, 2010.

Schneider et al., The effector T cells of diabetic subjects are resistant to regulation via CD4+ FOXP3+ regulatory T cells. J Immunol. Nov. 15, 2008;181(10):7350-5.

Thornton et al., Heterogeneous effects of IL-2 on collagen-induced arthritis. J Immunol. Aug. 1, 2000;165(3):1557-63.

A

B

USE OF LOW DOSE IL-2 FOR TREATING AUTOIMMUNE-RELATED OR INFLAMMATORY DISORDERS

RELATED APPLICATIONS

This application is a continuation of and claims priority under 35 U.S.C. § 120 to U.S. application Ser. No. 16/361,902, filed Mar. 22, 2019, which is a continuation of and claims priority under 35 U.S.C. § 120 to U.S. application Ser. No. 15/588,226, filed May 5, 2017, which is a continuation of and claims priority under 35 U.S.C. § 120 to U.S. application Ser. No. 14/004,211, filed Sep. 10, 2013, which is a national stage filing under 35 U.S.C. § 371 of international PCT application PCT/EP2012/054174, filed Mar. 9, 2012, which claims priority from European Patent Application 11305269.0 filed Mar. 11, 2011 and U.S. Provisional Application 61/451,663 filed Mar. 11, 2011, each of which is herein incorporated by reference in its entirety.

FIELD OF THE INVENTION

The present invention relates to novel IL-2-based therapies of human diseases. More specifically, the present invention relates to low doses IL-2 therapies of autoimmune, immune-related, or inflammatory diseases including inflammation in human subjects.

BACKGROUND OF THE INVENTION

Interleukin-2 (IL-2) was identified almost 30 years ago [1] and originally called T cell growth factor because of its ability to stimulate T lymphocytes in vitro. It is a protein with a reported molecular weight of between approx. 13 kda and 17 kda [2] and an isoelectric point of approx. 6 to 8.7.

IL-2 has been used in the clinic for boosting effector immune responses in cancers and infectious diseases [3, 4]. It is now authorized for use in human for the treatment of cancer.

In one of its registered indications, adjunct treatment of renal cell carcinoma (RCC), less than 10% of the patients respond to treatment. This limited efficacy of IL-2 is now partly explained by the recent discovery that IL-2 also plays a major role in the peripheral survival and suppressive function of regulatory T cells (Tregs) [5, 6], which are known to suppress anti-tumor effector responses.

In fact, IL-2/IL-2 receptor (IL-2R) signalling is important during immune responses of both effector T cells (Teff) and Treg. On the one hand, extensive IL-2R signalling is necessary for the development of terminally differential short-lived Teff cells that exhibit enhanced functional activity, and for eliciting proper T cell memory [7]. On the other hand, IL-2/IL-2R signalling is essential for Treg development and homeostasis as shown by the fact IL-2 knock-out mice lack Tregs. Noteworthy, IL-2 or IL-2R deficient mice are able to mount effector immune responses, as notably attested by their development of severe T-cell mediated auto-immune diseases (AID).

These different consequences of IL-2 signalling abnormalities are now explained by the fact that both quantitative and qualitative differences in IL-2/IL-2R signalling regulate Treg and Teff. Tregs appear to require low IL-2/IL-2R signalling threshold to support their development and peripheral homeostasis [6]. IL-2 administration has been shown to lead to marked expansion and activation of Tregs in mice and humans [3, 4, 8].

Nowadays, IL-2 continues to be utilized exclusively for cancer immunotherapy, and has not been investigated in human auto-immune diseases or, more generally, in human diseases caused by an undesirable immune response. This is because of the perceived and expected risks associated with such treatment. Indeed, the capacity of IL-2 to stimulate Teffs carries the risk of activating the very effector T cells that mediate the disease and therefore to aggravate the disease.

SUMMARY OF INVENTION

An object of the invention relates to a method for reducing or preventing an undesirable immune response in a human subject, the method comprising administering to said subject an amount of interleukin-2 (IL-2) efficient to stimulate regulatory T lymphocytes (Tregs) without substantially inducing effector T lymphocytes (Teffs).

A further object of the invention relates to a method for reducing or preventing an undesirable immune response in a human subject, the method comprising administering to said subject an amount of interleukin-2 (IL-2) efficient to stimulate regulatory T lymphocytes (Tregs) without substantially inducing IL-2-associated side effects.

A further object of the invention relates to a method for reducing or preventing an undesirable immune response in a human subject, the method comprising administering to said subject an amount of interleukin-2 (IL-2) efficient to stimulate regulatory T lymphocytes (Tregs) without substantially inducing effector T lymphocytes (Teffs) and IL-2-associated side effects.

A further object of the invention relates to a method for reducing or preventing an undesirable immune response in a human subject, the method comprising administering to said subject an amount of interleukin-2 (IL-2) efficient to shift the balance (or ratio) between regulatory T lymphocytes (Tregs) and effector T lymphocytes (Teffs) (Treg/Teff balance) towards Tregs in said subject.

A further object of the invention relates to a method for reducing or preventing an undesirable immune response in a human subject, the method comprising administering to said subject an amount of interleukin-2 (IL-2) efficient to increase the balance (or ratio) between regulatory T lymphocytes (Tregs) and effector T lymphocytes (Teffs) in said subject.

The present invention proposes novel IL-2-based therapies. The invention shows, for the first time, that IL-2 can be used as a novel class of immuno-regulatory and anti-inflammatory drugs acting by specific Treg expansion/activation.

A further object of the invention relates to a method for treating an autoimmune, immune-related or inflammatory disorder in a human subject, the method comprising administering to said subject an amount of interleukin-2 (IL-2) efficient to shift the balance between regulatory T lymphocytes (Tregs) and effector T lymphocytes (Teffs) (Treg/Teff balance) towards Tregs in said subject.

A further object of the invention relates to a method for treating an autoimmune, immune-related or inflammatory disorder in a human subject, the method comprising administering to said subject an amount of interleukin-2 (IL-2) efficient to stimulate regulatory T lymphocytes (Tregs) without substantially inducing effector T lymphocytes (Teffs), and/or to decrease inflammation.

The invention may be used for curative or preventive treatment of such disorders. More particularly, the methods of the invention prevent occurrence or development of an autoimmune, immune-related or inflammatory disorder in a subject.

IL-2 is typically administered repeatedly.

Interleukin-2 for use in treating an autoimmune, an immune-related or an inflammatory disorder according to claim 1, wherein it is to be administered at a dose of about 0.05 to about 2 millions international unit (MIU)/m$^2$/day, preferably about 0.1 or 0.2 to about 1 MUI/m$^2$/day or at a dose of less than about 3.5 MIU/day.

In a preferred embodiment, it is administered at a dose of about 3 MIU/day or at a dose of less than about 2 MIU/day, preferably at a dose of between about 0.1 MIU and about 2 MIU/day, preferably of between about 0.3 MIU and about 1 MIU/day.

The treatment may preferably comprise at least a first course wherein interleukin-2 is administered once per day during at least 3 consecutive days, preferably during 3 to 7, still preferably 4 to 5 consecutive days. Preferably it is followed by a maintenance dose after two to four weeks. The maintenance dose can be administered once a week, or once or twice a month.

In a preferred embodiment, the treatment comprises at least a first course wherein a dose of about 0.2 MUI/m$^2$ of interleukin-2 is administered once a day during at least 3 consecutive days, preferably during 3 to 7, still preferably 4 to 5 consecutive days, followed by a maintenance dose of about 0.2 MUI/m$^2$ after one to three weeks, which maintenance dose can be repeated every one to three weeks. In a preferred aspect, the subject is an adult that is administered with about 0.3 MUI as the daily dose of 0.2 MUI/m$^2$.

In another preferred embodiment, the treatment comprises at least a first course wherein a dose of about 0.6 MUI/m$^2$ of interleukin-2 is administered once a day during at least 3 consecutive days, preferably during 3 to 7, still preferably 4 to 5 consecutive days, followed by a maintenance dose of about 0.6 MUI/m$^2$ after two to 4 weeks, which maintenance dose can be repeated every two to four weeks. In a preferred aspect, the subject is an adult that is administered with about 1 MUI as the daily dose of 0.6 MUI/m$^2$.

In still another preferred embodiment, the treatment comprises at least a first course wherein a dose of about 1.8 MUI/m$^2$ of interleukin-2 is administered once a day during at least 3 consecutive days, preferably during 3 to 7, still preferably 4 to 5 consecutive days, followed by a maintenance dose of about 1.8 MUI/m$^2$ after about one to two months, which maintenance dose can be repeated every one to two months. In a preferred aspect, the subject is an adult that is administered with about 3 MUI as the daily dose of 1.8 MUI/m$^2$.

Generally speaking, it is preferred that IL-2 is administered at a dose of D/10 to 20×D, preferably D/5 to 10×D, wherein D is the minimal dose triggering up-regulation of expression of CD25 in Treg, without inducing expansion of Treg. Preferably the up-regulation of expression of CD25 is at least 33%, preferably at least 50%.

The invention stimulates regulatory T lymphocytes (Tregs) without substantially inducing effector T lymphocytes (Teffs) in a human subject. The methods of the invention make it possible to increase the Treg/Teff balance or to increase potent suppressive Treg cell population in said subject.

IL-2 is further administered for reducing or preventing inflammation in a human subject.

The invention may be used for the treatment or prevention of any condition associated to or caused by an undesirable immune response. It is particularly suited for treating inflammatory, immune-related or autoimmune diseases, including without limitation HCV-related vasculitis, uveitis, myositis, type I diabetes, systemic lupus erythematous, systemic vasculitis, psoriasis, allergy, asthma, Crohn's disease, Multiple Sclerosis, Rheumatoid Arthritis, atherosclerosis, autoimmune thyroid disease, neuro-degenerative diseases, Alzheimer disease, graft-versus-host disease, spontaneous abortion and allograft rejection.

Another subject of the invention is a method for determining whether a IL-2 regimen or dose has to be modified in a patient with an autoimmune, an immune-related or an inflammatory disorder, treated with IL-2, which method comprises monitoring the quantity of Tregs and/or CD25 expression level in Tregs, wherein a quantity of Tregs and/or CD25 expression level in Tregs inferior to a control value, means that the dose of IL-2 is to be increased.

LEGEND TO THE FIGURES

FIG. 1: Effects of low dose IL-2 on biological markers of HCV related autoimmune vasculitis Time course changes in HCV viral load (panel A), cryoglobulin (panel B) and C4 complement serum levels (panel C) are shown. Data are expressed as mean±standard errors (n=10, *: P<0.05, P<0.01, *: P<0.001).

Figure 2:
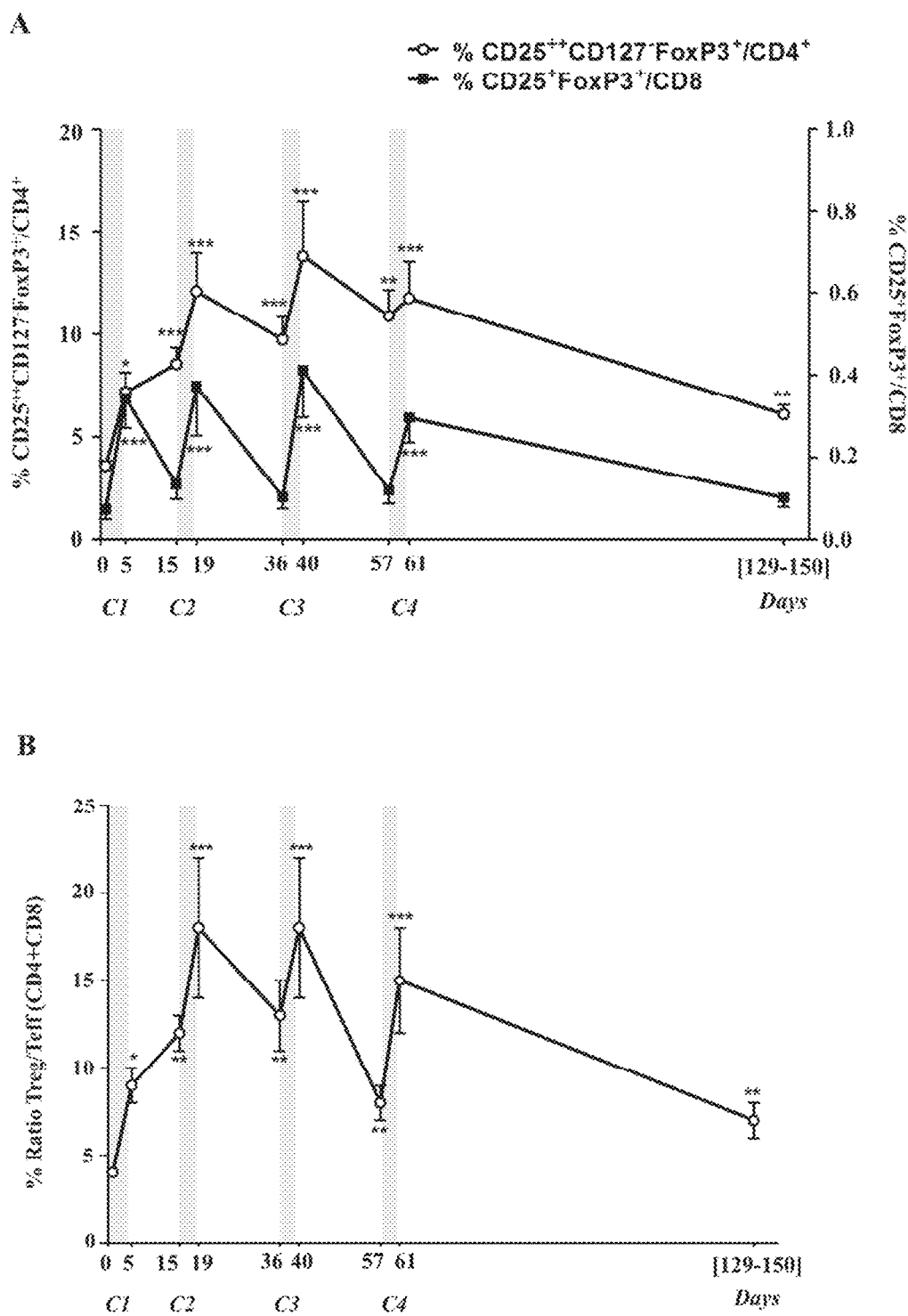
Figure 2:
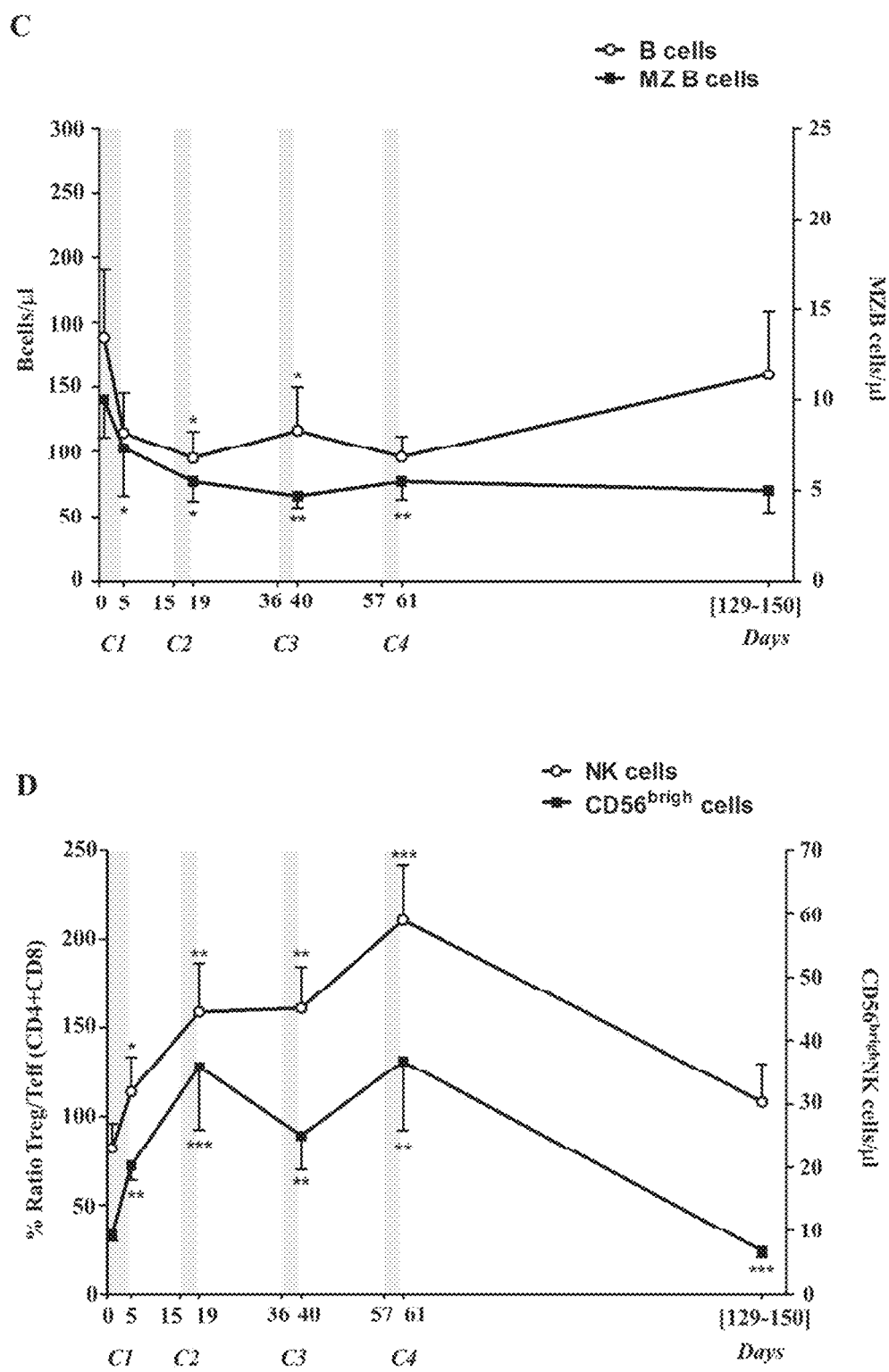

FIG. 2: Effects of low dose IL-2 on lymphocyte sub populations

Time course changes of percentages of CD4$^+$ CD25$^{hi}$CD127$^-$Foxp3$^+$ in CD4$^+$ T cells and of CD8$^+$CD25$^+$ Foxp3$^+$ in CD8$^+$ T cells (panel A), global Treg/Teff ratio (panel B), absolute numbers of CD19$^+$ total B cells and Marginal zone B cells (panel C) and of NK cells and CD56$^{bright}$ NK cells (panel D) are shown. Data are expressed as mean±standard errors (n=10, *: P<0.05, P<0.01, *: P<0.001).

Figure 3:
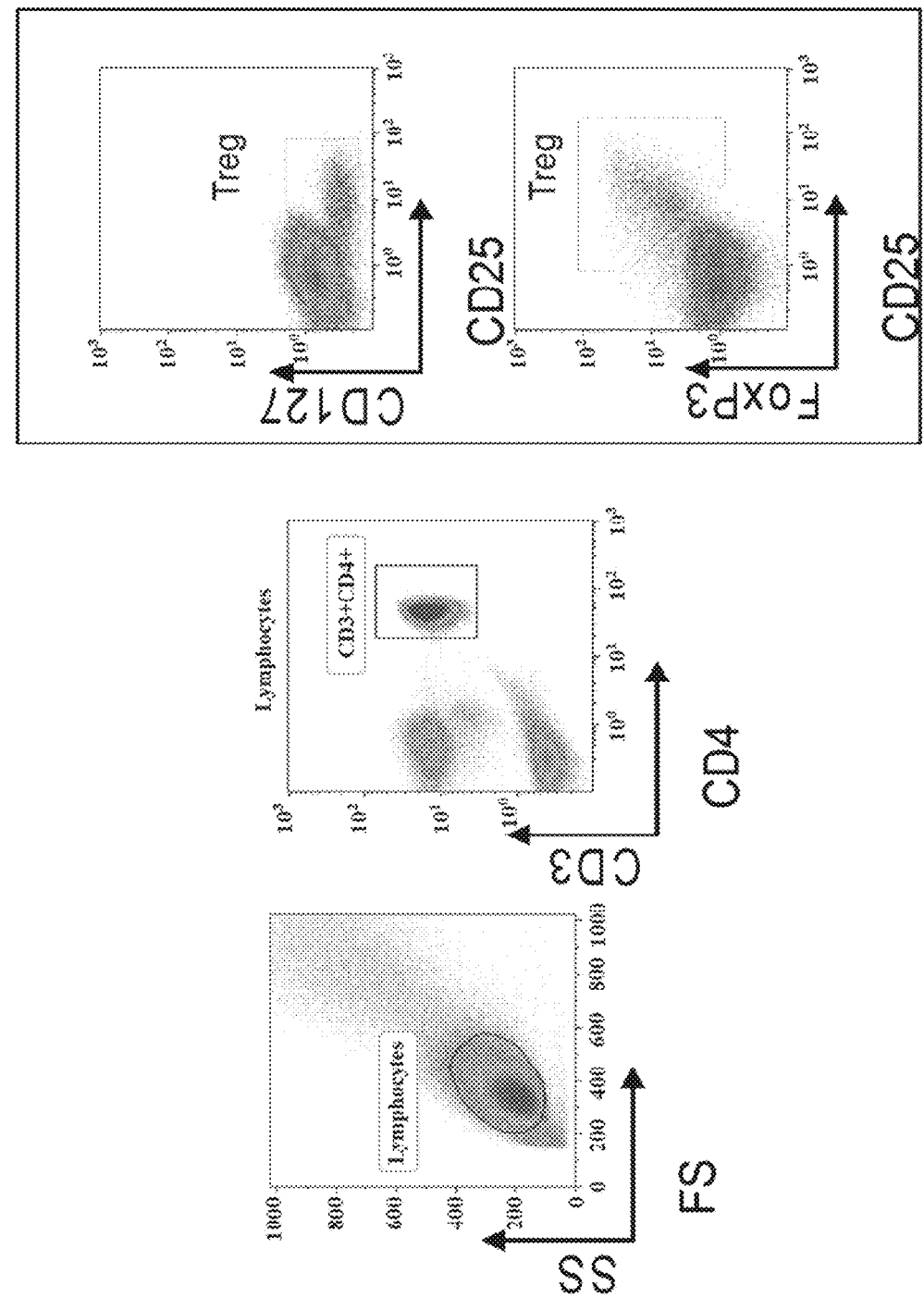

FIG. 3. Phenotypic characterization of CD4$^+$ Treg by Flow cytometry. Representative lymphocyte gate for identification of the CD3$^+$CD4$^+$ T subset is shown. Within the CD3$^+$CD4$^+$ T cells, Tregs were identified as CD25$^{high}$CD127$^-$FoxP3$^+$ cells.

Figure 4:
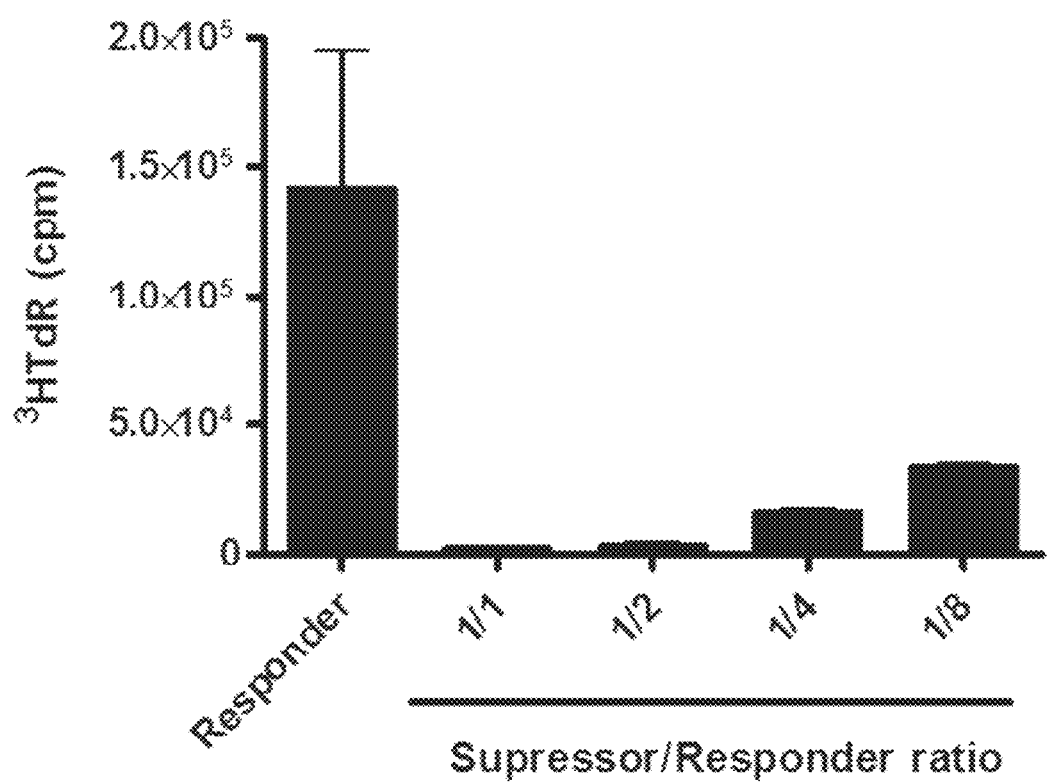

FIG. 4. Suppressive activity of Treg cells in HCV related autoimmune vasculitis patients under IL-2 treatment FACS purified Treg were assayed for their capacity to suppress autologous effector T cells proliferation at different ratios (1/1 to 1/8) under allogeneic stimulation. Results are expressed in cpm. The experiment shown is representative of 4.

Figure 5:
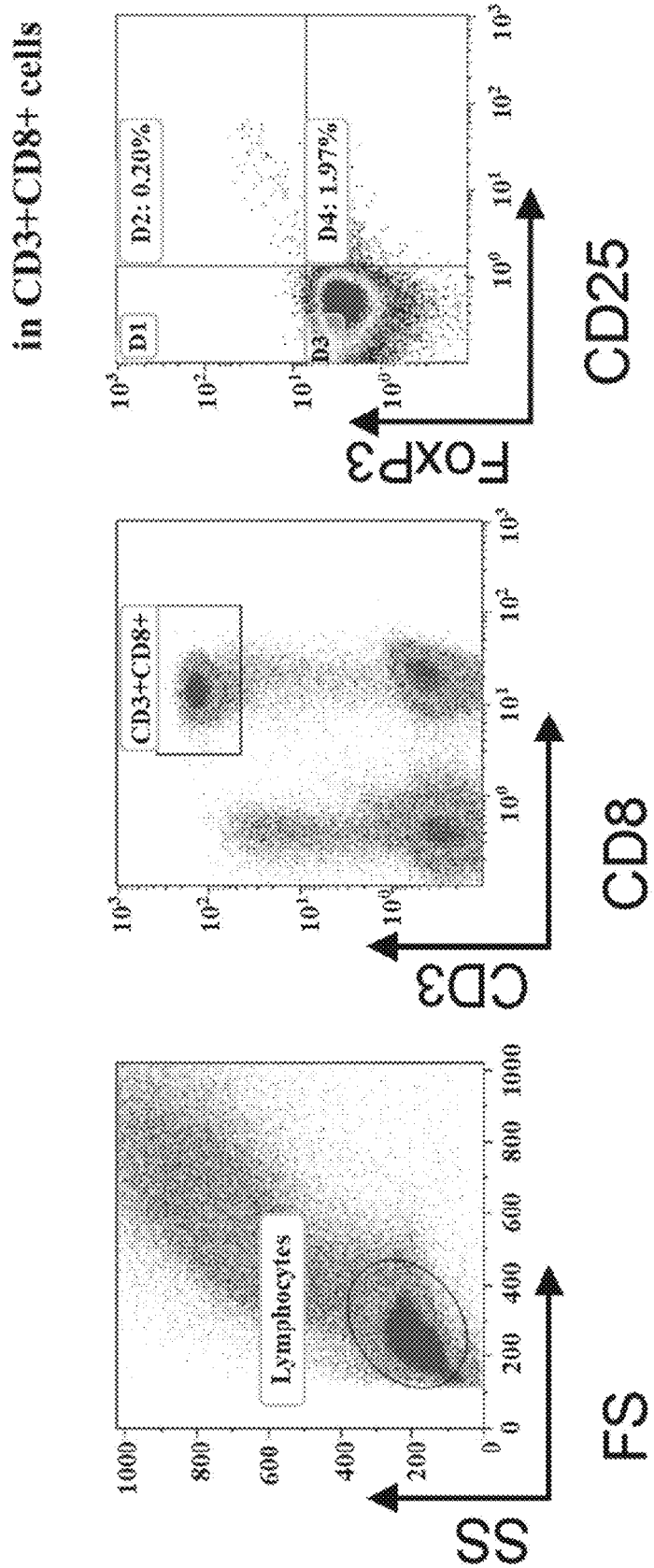

FIG. 5. Phenotypic characterization of CD8$^+$ Treg by Flow cytometry. Representative lymphocyte gates for the identification of CD3$^+$CD8$^+$ Treg are shown. Within CD3$^+$ CD8$^+$ T cells, Tregs were identified as CD25$^+$ FoxP3$^+$ cells.

Figure 6:
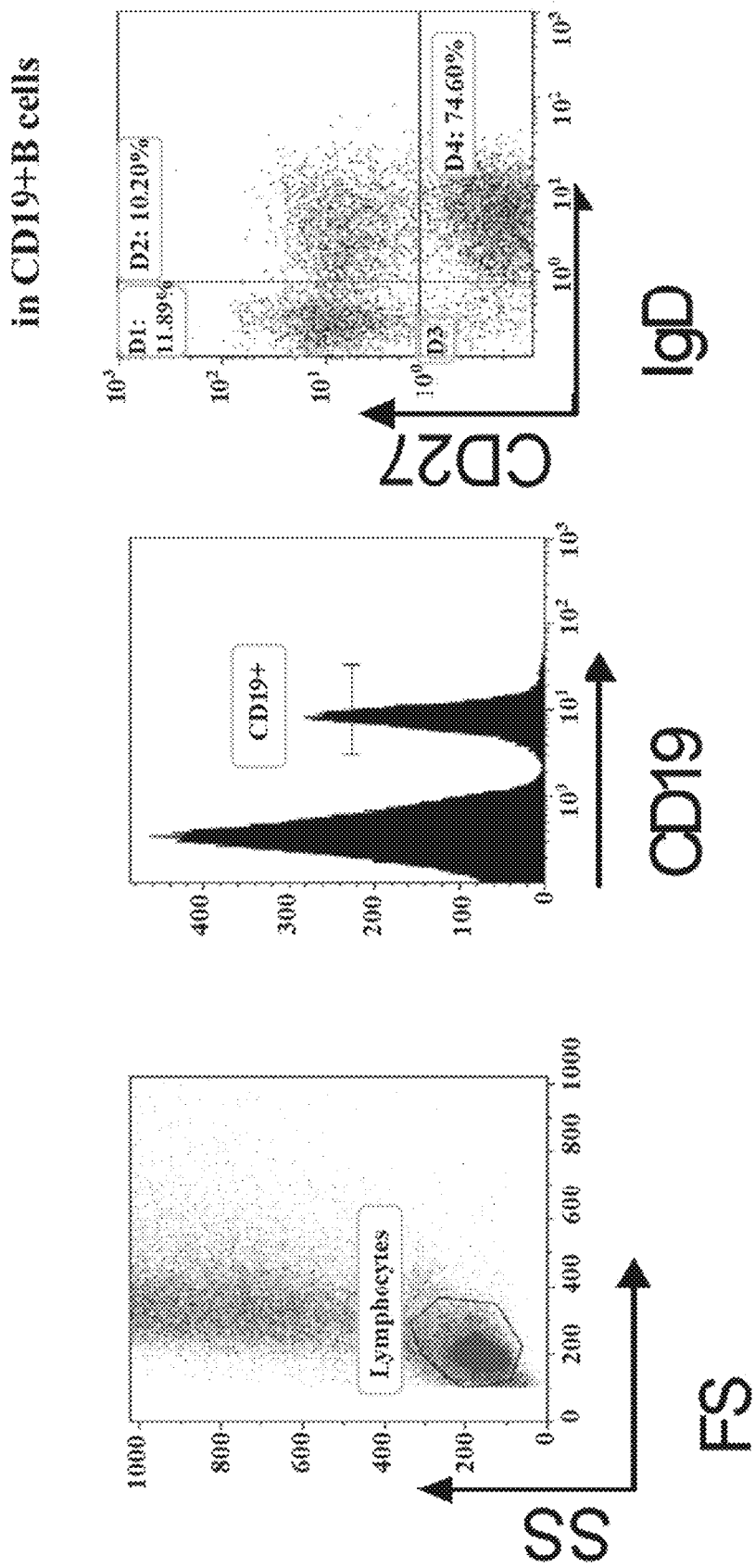

FIG. 6. CD19$^+$ B cells subsets characterization by flow cytometry

B cell subset populations were defined as naïve (IgD$^+$ CD27$^-$), memory (IgD$^-$CD27*), marginal zone (IgD$^+$ CD27+).

Figure 7:
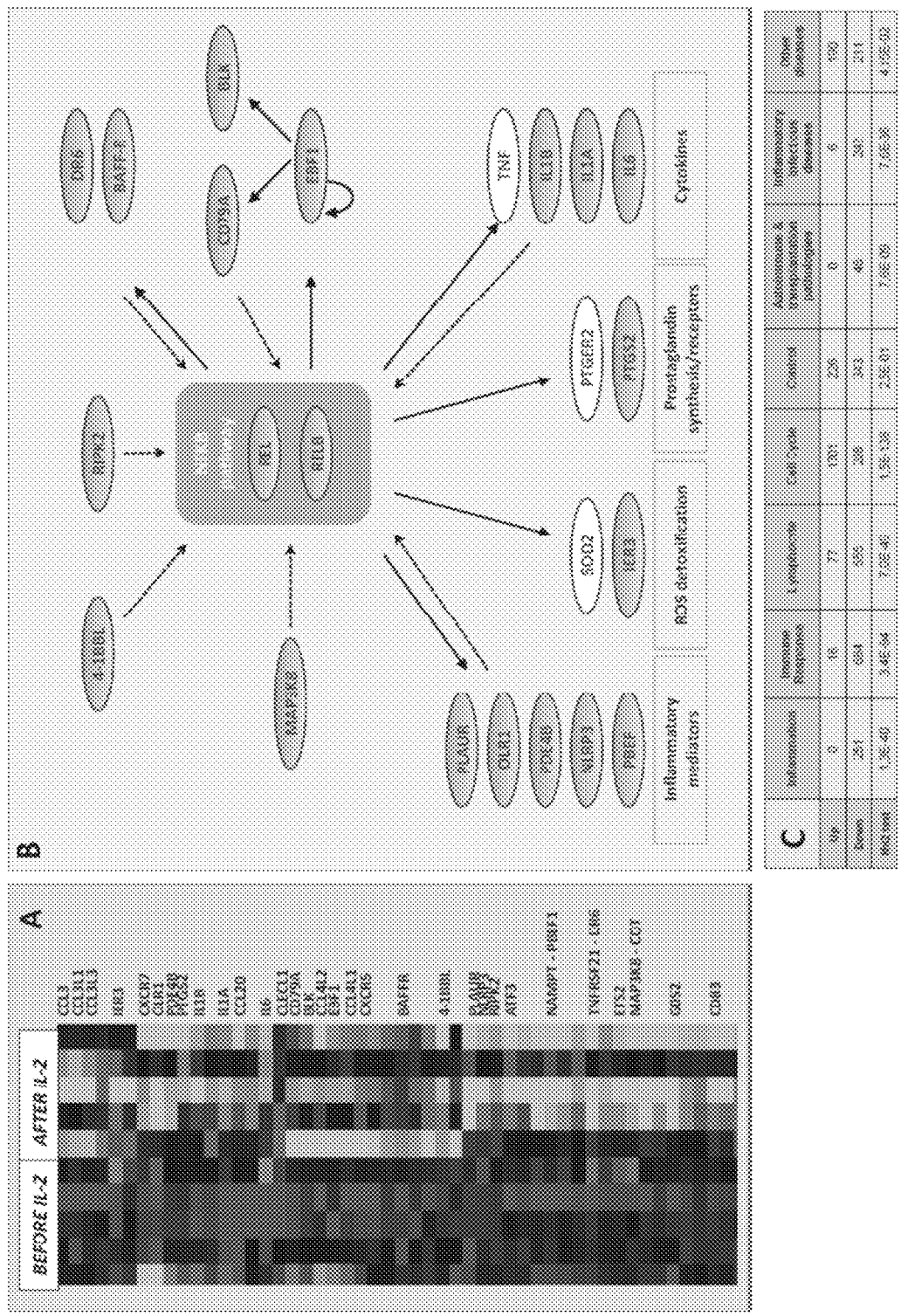

FIG. 7: Low dose IL-2 induces a global decrease of inflammation revealed by transcriptome analyses of PBMCs Hierarchical clustering before and after IL-2 treatment (panel A) highlights gene downregulations affecting mainly B cell related genes and proinflammatory genes. Data mining identified the NFKB pathway as central in the decreased proinflammatory response (panel B). Down-regulated genes in IL-2 treated patients are symbolized in red boxes. Genes present in the transcriptional signature (panel A) are schematically represented in filled round-boxes. Post-transcriptional activation between 2 gene products (e.g. by phosphorylation, clivage etc. . . . ) is represented with a sharp arrow and a filled arrow stands for a direct transcriptional activation. Dotted arrows represent indirect signalling.

The table (panel C) shows the results of an ICA of these data. Number of up- or down-regulated signatures in the IL-2-treated group that have significant enrichment for GO terms and KEGG pathways related to inflammation, immune response, and autoimmune (type I diabetes mellitus, systemic lupus erythematosus, autoimmune thyroid disease), transplantation (graft-versus-host disease and allograft rejection) or inflammatory infection-related pathologies (Chagas disease, Leishmaniasis, *Helicobacter pylori* infection, Malaria, Amoebiasis, Shigellosis, all characterized by a high degree of inflammation) are shown. As controls, the same number of randomly-picked GO terms was tested, together with cell-cycle related GO terms and control pathologies. For each GO term or KEGG pathway, the Khi2 test p-value indicates a possible enrichment bias for up- or down-regulated signatures as compared to the overall up- (2527) or down- (3429) regulated signatures.

Figure 8:
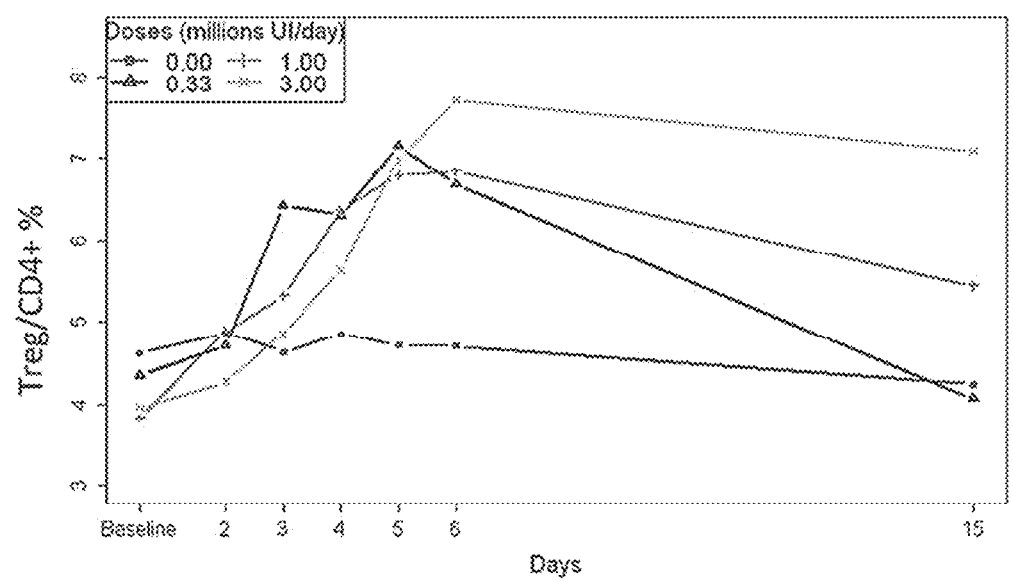

FIG. 8: Low dose IL-2 induces Treg in Type I diabetes patients.

FIG. 8 shows the Treg/$T_{CD4}$ ratio in patients administered with 0.33, 1 or 3 MUI/day IL-2 (Proleukin®) during 5 days. The peak Treg increase is relatively similar at the different doses, but the duration of the effect is dose-dependent, and provides information to define the schedule of the maintenance treatment (i.e. the lower the dose, the shorter the delay between maintenance injections).

Figure 9:
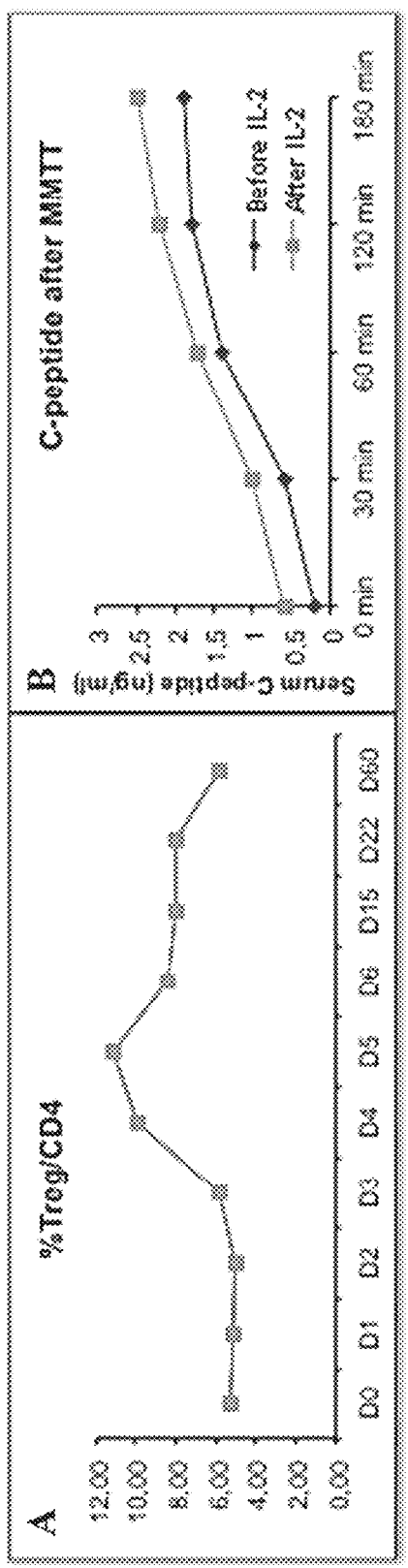

FIG. 9: Low dose IL-2 did not decrease C-peptide production.

FIG. 9A shows the Treg/$T_{CD4}$ ratio in a patient administered with IL-2 (Proleukin®) during 5 days. FIG. 9B shows the concentration of serum C-peptide before and after administration of IL-2, in the same patient. There is an increase in Treg during treatment, which correlates with an increase in C peptide production at 2 months.

DETAILED DESCRIPTION OF THE INVENTION

The present invention unexpectedly shows, for the first time, in vivo expansion of very potent suppressive Tregs without expansion of Teff nor occurrence of adverse events through low-dose IL-2 immunotherapy in human autoimmune patients.

IL-2 is utilized exclusively for cancer immunotherapy, and has not been investigated alone in human auto-immune diseases in humans. Indeed, the capacity of IL-2 to stimulate Teffs carries the risk of activating the very effector T cells that mediate auto-immunity. Here, we show biological evidence that IL-2 can be used under conditions that induce Tregs without inducing Teffs, concordant with clinical evidence showing that no immune activation-related adverse events were observed. In accordance with this invention, IL-2 clearly tips the Treg/Teff balance in favor of Tregs, as also supported by the globally reduced inflammatory context during IL-2 therapy.

In first trials in HCV-related patients, the inventors showed that low-dose IL-2 is well tolerated, induces a dramatic and selective increase in Treg cells, and leads to clinical improvement in 80% of the patients.

With a 5-day 1.5 M IU/day course treatment, a significant increase of Treg was observed in all patients (a 2 fold increase), with no side effects. After additional 5-day courses of 3 M IU/day, a further increase of Tregs was noted.

Our results show the treatment was well tolerated, with no significant changes in granulocytes, red blood cells, or liver enzymes. Furthermore, at the dosage of 1.5 MIU/day, no side effects were noted such as asthenia, transient local reactions at injection sites, flu-like syndrome, myalgia or hypertension.

Importantly, during the entire treatment and follow-up, there were no biological or clinical signs indicating activation of pathogenic T cells.

A course of 1.5 M IU/day for 5 days represents so far the lowest IL-2 dose with proven efficacy and safety for Tregs induction purposes in humans.

In addition, the present invention revealed, for the first time, a marked anti-inflamatory activity of IL-2. Our unsupervised transcriptome analyses showed a clear down-regulation of signatures/pathways associated with many autoimmune and inflammatory diseases, as well as immune-related diseases such as graft versus host disease and allograft rejection. With this study showing that it is possible to use IL-2 to stimulate Treg without stimulating Teff in humans, the inventors propose that low dose IL-2 treatments will profoundly change the preventive and therapeutic paradigms for all these diseases.

The inventors have proceeded further with testing low-dose IL-2 in another autoimmune disease, namely type I diabetes, thereby confirming the interest of low-dose IL-2 in treating autoimmune, immune-related or inflammatory disorders.

The present invention therefore provides new therapeutic approaches for treating autoimmune, immune-related or inflammatory disorders using IL-2. The invention discloses that IL-2, at low doses, can effectively activate or expand suppressive Treg cell population in subjects having autoimmune, immune-related or inflammatory disorders, without substantially activating effector T cells.

The subject is any human patient, regardless of age or gender. In a particular embodiment, the patient may be a child, or an adolescent.

Interleukin-2 (IL-2)

Within the context of this invention, the term "IL-2" designates any source of IL-2, including mammalian sources such as e.g., human, mouse, rat, primate, and pig, and may be native or obtained by recombinant or synthetic techniques, including recombinant IL-2 polypeptides produced by microbial hosts. IL-2 may be or comprise the native polypeptide sequence, or can be an active variant of the native IL-2 polypeptide. Preferably the IL-2 polypeptide or active variant is derived from a human source, and includes recombinant human IL-2, particularly recombinant human IL-2 produced by microbial hosts.

Active variants of IL-2 have been disclosed in the literature. Variants of the native IL-2 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide.

Methods for determining whether a variant IL-2 polypeptide is active are available in the art and are specifically described in the present invention. An active variant is, most preferably, a variant that activates Tregs.

Examples of IL-2 variants are disclosed, for instance, in EP109748, EP136489, U.S. Pat. No. 4,752,585; EP200280, or EP118,617.

Preferably we use a recombinant IL-2, i.e., an IL-2 that has been prepared by recombinant DNA techniques [9]. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. Nos. 4,656,132; 4,748,234; 4,530,787; or U.S. Pat. No. 4,748,234, incorporated therein by reference.

In a preferred embodiment, the invention uses an IL-2 of human origin, or an active variant thereof, more preferably produced recombinantly. A nucleotide and an amino acid sequence of human IL-2 are disclosed, for instance, in Genbank ref 3558 or P60568, respectively. The invention more preferably uses a human IL-2.

IL-2 for use in the present invention shall be in essentially pure form, e.g., at a purity of 95% or more, further preferably 96, 97, 98 or 99% pure.

For use in the present invention, IL-2 is typically not combined or co-administered with a Teff suppressive agent. However, although not preferred or required, drug combinations may be contemplated.

IL-2 may be used in monomeric or multimeric form.

IL-2 is commercially available, including for pharmaceutical uses, and it is authorized for use in human patients. Suitable commercial forms include, e.g., Proleukin®, a recombinant, human IL-2 composition, Aldesleukin®, an unglycosylated des-alanyl-1, serine-125 human interleukin-2 produced in *E. coli*.

Roncoleukin®, recombinant human IL-2 produced in yeast.

Interleukin-2 may be used alone or in combination with any other therapeutically active agent. In a preferred embodiment, when IL-2 is not administered in combination with rapamycin when used in preventing or treating type I diabetes.

Regulatory T Cells

Regulatory T cells are T lymphocytes having immunosuppressive activity. Natural Tregs are characterized as CD4+CD25+Foxp3+ cells. Humans and mice presenting a genetic deficit in Tregs develop multiple T-cell mediated organ-specific autoimmune diseases. A Treg quantitative or qualitative defect has been described in many human autoimmune diseases, including systemic lupus erythematosis (SLE), Type 1 Diabetes, Multiple Sclerosis, uveitis and myositis. Conversely, addition/restoration of Treg induces clinical improvements in most animal models of these diseases.

Tregs also play a major role in the control of inflammatory diseases, although their mode of action in such disease is not well understood. In fact, in most inflammatory diseases, Treg depletion exacerbates disease while Treg addition decreases it. This is for example shown in the context of atherosclerosis. Although this disease is not primarily an inflammatory disease, its development involves an inflammatory component/loop. In apolipoprotein E (ApoE) deficient mice that spontaneously develop atherosclerosis, Treg depletion significantly aggravated the plaque formation, while injection of polyclonal Tregs significantly improved the disease.

Most Tregs are CD4+ cells, although there also exists a rare population of CD8+Foxp3+ T lymphocytes with a suppressive activity.

Effector T Cells

Within the context of this application, "effector T cells" (or "Teff") designates conventional T lymphocytes other than Tregs (sometimes also referred to as Tconv in the literature), which express one or more T cell receptor (TCR) and perform effector functions (e.g., cytotoxic activity, cytokine secretion, anti-self recognition, etc). Major populations of human Teff according to this invention include CD4+ T helper lymphocytes (e.g., Th0, Th1, Th17) and CD4+ or CD8+ cytotoxic T lymphocytes, and they can be specific for self or non-self antigens.

In the particular situation of an autoimmune disease, the Teff cells include the T cell population responsible for or involved in the disease. For instance, such population of T cells include T lymphocytes which recognize a self antigen such as a thyroid antigen, a joint antigen, a 6-Langherans islet antigen, etc. In a GVHD disease, the Teff cells include T lymphocytes from the graft.

Selective Amplification of Tregs

Within the context of this invention, a stimulation (or induction or activation or amplification) of Treg designates any increase in proportion of Treg cells relative to Teffs, in number or in activity as tested by suppressive assays or by expression of molecules that reflect the activity of the Tregs such as CD25, the alpha-chain of the IL-2 receptor, in a patient. The augmentation in proportion is preferably by at least 20% as compared to the level prior to treatment, more preferably at least 40%, even more preferably at least 60%. In a particular and preferred embodiment, the stimulation designates a shift in the Treg/Teff balance towards Tregs, or an increase in the Treg/Teff ratio.

An essential aspect of the invention lies indeed in the ability, in vivo, in human patients having an autoimmune, immune-related or inflammatory disorder, to stimulate Tregs without substantially inducing Teff.

The induction (or activation or expansion) of Tregs can be measured as disclosed in the examples, e.g., by measuring the number of Tregs (e.g., based on the expression of CD25, FoxP3 . . . ) and/or the activity of Tregs in samples from the treated subject. The absence of substantial induction (or activation or expansion) of Teff can also be measured as disclosed in the examples, e.g., by measuring the number of Teff and/or the activity of Teff in samples from the treated subject. Preferably, the absence of substantial induction indicates the target Teff cell population does not acquire markers of activation such as CD25, CD69, and/or HLA-DR, or as assessed by whole transcriptome analyses. Detailed methods for detecting, measuring and quantifying Treg and Teff cells are well known per se in the art and some are disclosed in the examples.

Stimulation in Tregs may be measured by an increase in Treg counts in the patient, typically by 10% at least, or by an increase in activation markers such as the intensity of CD25 expression. The absence of Teff induction typically designates that the Teff cell population has not increased by more than 10% in said subject as a result of treatment.

The stimulation of Treg and absence of substantial induction of Teff is preferably assessed by a measure of the ratio or the balance Treg/Teff in the treated subject. This balance is calculated e.g., based on the number of Tregs and the number of Teff in a sample from the subject. As illustrated in the examples, such a balance typically increases by at least 20% in the treated patients, more preferably by at least 30%, 40% or 60%.

The baseline percentage of Tregs in human subjects, i.e., the ratio of Tregs/CD4+ Teffs, is approx. 4.6±0.6% (the baseline % in patients with autoimmune disease may be much lower, as shown in Example 1, where patients with HCV-induced autoimmune vasculitis had a baseline percentage level of 3.6%±0.23 only, although these numbers may vary from one laboratory to another, based on technical aspects of the measurement).

The results presented in this application show that, after 1 course of treatment with 1.5 MIU/day, a 2-fold (100%) increase in the baseline % of Tregs is obtained, which may be further amplified upon additional treatment. Depending on the protocol, increases above 300% have been obtained. A similar 2-fold increase after 1 5-Day course has been observed in patient with T1D, whatever the dose used (0.33; 1 and 3 MIU/day).

In a preferred embodiment, the method allows an increase by 20%, 30%, 40%, 50%, 75%, 100% or more of the Treg/Teff ratio in a subject.

Furthermore, the invention shows an increase not only in CD4+ Tregs, but also in a rare population of Tregs which are CD8+.

In a particular embodiment, the invention increases circulating CD4$^+$CD25$^{hi}$CD127$^-$Foxp3$^+$ Tregs.

In another particular embodiment, the invention increases circulating CD8$^+$CD25$^{hi}$Foxp3$^+$ Tregs.

Another important aspect is that the amplified Treg cell population is highly suppressive. Indeed, the results presented show that, upon treatment according to the invention, Tregs are activated having a potent suppressive activity towards Teff cells. In our study, a substantial suppressive activity (>75%) could be detected at Treg/Teff ratio of 1/8 in a classical suppressive assay in which Treg from non treated normal individual gives such a suppression at ratio of ½ to ¼.

The invention therefore allows a substantial increase in Tregs in human subjects having autoimmune diseases, without substantial alteration or activation of effector T lymphocytes. In a preferred embodiment, the method of the invention is a method that increases by at least 30% the CD25$^+$Foxp3$^+$ Tregs in a subject and that causes less than 5% increase in target Teffs in said subject.

Also, the invention unexpectedly shows that, at preferred administration doses, the IL-2-based therapies of the invention essentially do not induce arterial hypertension; headaches, nausea, arthralgia, myalgia, or Flu-like syndrome, nor many other IL-2 known side effects as described in the IL-2 Summary of Product Characteristics of the FDA). It is therefore possible to use IL-2 therapy in human subjects having immune-related disorders, without substantially activating Teff cells and without substantially inducing IL-2-associated side effects, while very substantially inducing Tregs and anti-inflammatory effect.

IL-2 Dosage

For use in the present invention, IL-2 is administered at a dosage which effectively activates Tregs without substantially activating Teffs. The consequence is a dramatic increase in the Treg/Teff balance in the subject.

The effective dosage can be adjusted by the practitioner, based on information contained in the present application. In particular, with the knowledge of the present invention that, in patients with autoimmune disease, IL-2 may be administered under conditions which do activate Tregs and which essentially do not activate Teff, the skilled person may be able to adjust dosages to each patient and condition.

Typically IL-2 is administered at a dose of about 0.05 to about 2 MIU/m$^2$/day, preferably 0.2 to about 1 MIU/m$^2$/day.

The amount of IL-2 to administer thus preferably depends on the body surface area of the subject. The body surface area (BSA) is the measured or calculated surface of a human body.

Various calculations have been published to arrive at the BSA without direct measurement:

The Dubois & Dubois formula [18] is commonly used in adults:

$$BSA(m^2) = 0.007184 \times \text{weight(kg)}^{0.425} \times \text{height(cm)}^{0.725}$$
$$= \frac{\text{weight(kg)}^{0.425} \times \text{height(cm)}^{0.725}}{139.2}$$

Another commonly used formula is the Mosteller formula [19] adopted for use by the Pharmacy and Therapeutics Committee of the Cross Cancer Institute, Edmonton, Alberta, Canada:

$$BSA(m^2) = \sqrt{\frac{\text{weight(kg)} \times \text{height(cm)}}{3600}} = \frac{\text{weight(kg)}^{0.5} \times \text{height(cm)}^{0.5}}{60}$$

It is more particularly used in children.

Average BSA is generally taken to be 1.73 m$^2$ for an adult.

| Average BSA values | |
| --- | --- |
| Neonate (Newborn) | 0.25 m$^2$ |
| Child 2 years | 0.5 m$^2$ |
| Child 9 years | 1.07 m$^2$ |
| Child 10 years | 1.14 m$^2$ |
| Child 12-13 years | 1.33 m$^2$ |
| For men | 1.9 m$^2$ |
| For women | 1.6 m$^2$ |

Typically, the dosage according to the invention is below 3.5 Million IU/day/patient, more preferably below 3.0 Million IU/day/patient, even more preferably below 2.5 Million IU/day/patient, further preferably below 2.0 Million IU/day/patient.

The treatment is typically repeated, i.e., the above low doses IL-2 are administered several times to a subject, to progressively achieve the most substantial benefit. The dose and schedule of administration vary according to the preventive or therapeutic aim of the treatment, as well as to the disease to be treated/prevented. Treatment effect can be monitored by Treg measurements and dose and administration schedule adjusted accordingly.

Examplary dosages are between 0.1 to 3 MIU, preferably 0.1 to 1.5 MIU, still preferably 0.25 to 1 MUI. Preferred dosages are:
3.0 M IU/day/patient,
2.5 M IU/day/patient,
2.0 M IU/day/patient,
1.5 M IU/day/patient,
1.0 M IU/day/patient,
0.5 M IU/day/patient,
0.3 MIU/day/patient
0.1 M IU/day patient,
0.05 M IU/day patient, 0.02 M IU/day patient, or
0.01 M IU/day patient.

These dosages may be combined, depending on the subject and evolution of the disease.

Treatment may be provided as courses of several days, e.g., 1-7 days of daily administration, preferably between 3 to 5 days. Such treatment courses may be reproduced at different time periods, interrupted by periods with no treatment. In a preventive setting, IL-2 may be administered at the above dosage in single shots, at different time intervals, e.g., once a week over long periods of time. Different protocols may be adjusted depending on the patient and disease. Maintenance dosage can be administered from two to eight weeks after the initiating cycle is completed. Preferably the maintenance dose is the same as the initiating dose.

Determination of Dosage:

Generally speaking, IL-2 may be administered at a dose of D/10 to 20×D, preferably D/5 to 10×D, wherein D is the minimal dose triggering induction of expression of CD25 in Treg, without inducing expansion of Treg.

This method for determining the appropriate low-dose of IL-2 is particularly useful when a route of administration different from the subcutaneous route is contemplated.

Especially such dosage may be useful in oral, nasal or rectal delivery.

Determination of CD25 levels can be accomplished using anti-CD25 antibodies in flow cytometry.

In this regard, lymphocyte-containing samples may be fixed with a suitable fixing agent (e.g. paraformaldehyde, which may be used at 1% in phosphate-buffered saline (PBS)) to permit the subsequent quantification or qualitative determination of the cell surface marker (e.g. by the use of flow cytometry) as convenient (e.g. following transport from the site of collection and culture of the lymphocyte-containing sample, to a flow cytometry laboratory). Commercially available Anti-CD25 monoclonal antibodies (mAbs) labeled to different fluorochrome such as Alexa488 (Molecular Probes, Oregon, USA) and FITC (Sigma) are available.

Examples of dose and administration schedules are given below.

Treatment of Type 1 Diabetes

Type 1 diabetes (T1D) is due to the auto immune destruction of the insulin-producing cells in the pancreas. In many patients a defect in the IL-2/IL-2 receptor activation pathway can be found. Furthermore, IL-2 can prevent the occurrence of type 1 diabetes in mouse models of T1D (NOD mice) and that IL-2 given very early after the onset of diabetes can reverse diabetes.

However, the occurrence of new onset of T1D has been described in patients with cancer treated with low dose of IL-2. Therefore the treatment of human TID patients with IL-2 is not straightforward and no one had yet started such a treatment with IL-2 alone. Example 2 shows the first results in a double blinded trial in T1D patients administered with low dose IL-2 (0.33, 1 or 3 MIU/day) during 5 days.

The inventors thus now disclose a method to 1) prevent and 2) treat T1D using low dose of IL-2, especially recent onset T1D.

Interleukin-2 is particularly recommended in a subject at risk of developing type I diabetes. In that case, the treatment with IL-2 is preventive of onset of the diabetes in said subject. In the setting of prevention, patient at risk of T1D (i.e. patients from family with a history of TID or patient with genetic polymorphism of the IL-2/IL-2 receptor activation pathway associated with higher frequency of T1D, and/or patients in whom auto-antibodies against antigens such as insulin, GAD, insulinoma-associated protein 2 (IA2), and tyrosine phosphatase or zinc transporter 8 (ZnT8) (or antibodies that have been associated with T1D) have been detected) are treated with low doses IL-2, thereby preventing the activation of the effector T cells that will generate T1D.

In this setting, the treatment uses doses of IL-2 equal or below 3 M IU/day, or even in a preferred embodiment below 1 or 0.5 M IU per day, and the treatment is administered once every two weeks, or preferably once every 3 weeks or preferably once every month. Treatment can be adjusted (dose or schedule) based on Treg proportion and function.

In another particular embodiment, a preferred candidate treat shows an underproduction of IL-2, and a residual production of insulin.

Indeed, in the therapeutic setting, our preferred use is for patients just diagnosed with T1D who are known to still have a remaining mass of insulin-producing cells in the pancreas. In a particular embodiment, Interleukin 2 in this setting can be given at a dose of 3 million units per day for 3 to 7 days and then additional IL-2 courses can be given at least once a month as described above. Treatment can be adjusted (dose or schedule) based on Treg proportion and function.

In a preferred embodiment, the treatment comprises at least a first course wherein a dose of about 0.2 MUI/m$^2$ of interleukin-2 is administered once a day during at least 3 consecutive days, preferably during 3 to 7, still preferably 4 to 5 consecutive days, followed by a maintenance dose of about 0.2 MUI/m$^2$ after one to three weeks, which maintenance dose can be repeated every one to three weeks. In a preferred aspect, the subject is an adult that is administered with about 0.3 MUI as the daily dose of 0.2 MUI/m$^2$.

In another preferred embodiment, the treatment comprises at least a first course wherein a dose of about 0.6 MUI/m$^2$ of interleukin-2 is administered once a day during at least 3 consecutive days, preferably during 3 to 7, still preferably 4 to 5 consecutive days, followed by a maintenance dose of about 0.6 MUI/m$^2$ after two to 4 weeks, which maintenance dose can be repeated every two to four weeks. In a preferred aspect, the subject is an adult that is administered with about 1 MUI as the daily dose of 0.6 MUI/m$^2$.

In still another preferred embodiment, the treatment comprises at least a first course wherein a dose of about 1.8 MUI/m$^2$ of interleukin-2 is administered once a day during at least 3 consecutive days, preferably during 3 to 7, still preferably 4 to 5 consecutive days, followed by a maintenance dose of about 1.8 MUI/m$^2$ after about one to two months, which maintenance dose can be repeated every one to two months. In a preferred aspect, the subject is an adult that is administered with about 3 MUI as the daily dose of 1.8 MUI/m$^2$.

The subcutaneous route is preferred.

Treatment and Prevention of Multiple Sclerosis Relapse.

Patient with multiple sclerosis (MS) can be treated with IL-2 to prevent or treat relapses. Patient with multiple sclerosis are prone to have relapse.

In a preferred embodiment, the treatment comprises at least a first course wherein a dose of about 0.2 MUI/m$^2$ of interleukin-2 is administered once a day during at least 3 consecutive days, preferably during 3 to 7, still preferably 4 to 5 consecutive days, followed by a maintenance dose of about 0.2 MUI/m$^2$ after one to three weeks, which maintenance dose can be repeated every one to three weeks. In a preferred aspect, the subject is an adult that is administered with about 0.3 MUI as the daily dose of 0.2 MUI/m$^2$.

In another preferred embodiment, the treatment comprises at least a first course wherein a dose of about 0.6 MUI/m$^2$ of interleukin-2 is administered once a day during at least 3 consecutive days, preferably during 3 to 7, still preferably 4 to 5 consecutive days, followed by a maintenance dose of about 0.6 MUI/m$^2$ after two to 4 weeks, which maintenance dose can be repeated every two to four weeks. In a preferred aspect, the subject is an adult that is administered with about 1 MUI as the daily dose of 0.6 MUI/m$^2$.

In still another preferred embodiment, the treatment comprises at least a first course wherein a dose of about 1.8 MUI/m$^2$ of interleukin-2 is administered once a day during at least 3 consecutive days, preferably during 3 to 7, still preferably 4 to 5 consecutive days, followed by a maintenance dose of about 1.8 MUI/m$^2$ after about one to two months, which maintenance dose can be repeated every one to two months. In a preferred aspect, the subject is an adult that is administered with about 3 MUI as the daily dose of 1.8 MUI/m$^2$.

In a particular setting of prevention according to this invention, a MS patient is treated with low doses IL-2 to prevent relapses. In this setting, the treatment uses doses of IL-2 equal or below 3 M IU/day, or even in a preferred embodiment below 1.5 M IU per day, and the treatment is administered once every two weeks, or preferably once every 3 weeks or preferably once every month. Treatment can be adjusted (dose or schedule) based on Treg proportion and function.

In the therapeutic setting, a MS patient undergoing a relapse can be given IL-2 at a dose of 3 million units per day for 5 to 7 days and then additional IL-2 courses can be given once a month as describe above. Treatment can be adjusted (dose or schedule) based on Treg proportion and function.

Prevention and Treatment of Atherosclerosis

Examples (non limiting) of uses are 1) for patients with moderate atherosclerosis, i.e. non symptomatic arterial stenosis who can receive monthly injection of low dose of IL-2 to prevent worsening of the condition; 2) for patients with aortic aneurysm who can receive monthly injection of low dose of IL-2 to prevent progressive increase of aneurysm size and worsening of the condition; 3) for patients with coronary or peripheral artery stenosis treated by angioplasty with/without stenting, to reduce inflammation and the risk of restenosis, IL-2 at a dose of 3 million units per day for 5 to 7 days and then additional IL-2 courses once a month; 4) after arterial bypass surgery to reduce inflammation and risk of restenosis, IL-2 at a dose of 3 million units per day for 5 to 7 days and then additional IL-2 courses once a month.

In a preferred embodiment, the treatment comprises at least a first course wherein a dose of about 0.2 MUI/m$^2$ of interleukin-2 is administered once a day during at least 3 consecutive days, preferably during 3 to 7, still preferably 4 to 5 consecutive days, followed by a maintenance dose of about 0.2 MUI/m$^2$ after one to three weeks, which maintenance dose can be repeated every one to three weeks. In a preferred aspect, the subject is an adult that is administered with about 0.3 MUI as the daily dose of 0.2 MUI/m$^2$.

In another preferred embodiment, the treatment comprises at least a first course wherein a dose of about 0.6 MUI/m$^2$ of interleukin-2 is administered once a day during at least 3 consecutive days, preferably during 3 to 7, still preferably 4 to 5 consecutive days, followed by a maintenance dose of about 0.6 MUI/m$^2$ after two to 4 weeks, which maintenance dose can be repeated every two to four weeks. In a preferred aspect, the subject is an adult that is administered with about 1 MUI as the daily dose of 0.6 MUI/m$^2$.

In still another preferred embodiment, the treatment comprises at least a first course wherein a dose of about 1.8 MUI/m$^2$ of interleukin-2 is administered once a day during at least 3 consecutive days, preferably during 3 to 7, still preferably 4 to 5 consecutive days, followed by a maintenance dose of about 1.8 MUI/m$^2$ after about one to two months, which maintenance dose can be repeated every one to two months. In a preferred aspect, the subject is an adult that is administered with about 3 MUI as the daily dose of 1.8 MUI/m$^2$.

Prevention of Repeated Spontaneous Abortion

Some couple experience difficulties in reproduction, with recurrent spontaneous abortion which are considered of immunological origin.

In a mouse model of recurrent abortion we have shown that administration of IL-2 prior to mating allow normal pregnancy outcome.

In female patients with recurrent spontaneous abortion, IL-2 can be given prior to a programmed conception or implantation of embryos obtained by in vitro fertilisation, to favor fetus implantation. As an example, IL-2 courses of 3 M IU per day for 5 days can be given a month to one week prior to a scheduled mating or implantation.

Prevention of Cell or Organ Rejection

After transplantation of potentially immunogenic allogenic cells or tissues or cell genetically modified with transgene, the administration of IL-2 according to this invention can be used to reduce the rejection rate.

Additional examples of Regimen for controlling flare:
Continuous 24 h infusion for 5 to 7 days at 0.1 to 3.5 or 3 M IU/day
Repeated dosing once daily for 5 to 30 days at daily dosage from 0.1 to 3.5 or 3 M IU/day
Repeated dosing once every two days for 15 to 30 days at daily dosage from 0.1 to 3.5 or 3 M IU/day
Repeated dosing once daily for 3 consecutive days in a week during 2 to 4 consecutive weeks at daily dosage from 0.1 to 3.5 M or 3 IU/day Examples of Regimen for Maintenance and/or Prevention:
Repeated dosing daily for one to seven day in a week every two to six weeks at daily dosage from 0.1 to 3.5 or 3 M IU/day
Repeated dosing once daily for 5 to 30 days every 3 to 6 month at daily dosage from 0.1 to 3.5 or 3 M IU/day
Repeated dosing once daily for 5 to 30 days once a year at daily dosage from 0.1 to 3.5 or 3 M IU/day.
Repeated dosing once daily for 1 to 3 days, every 1 to 3 months, at daily dosage from 0.1 to 3.5 or 3 M IU/day.
Maintenance dosing at 0.01 to 1 M IU/day, 1 day every weeks The need for administering multiple cycles of a constant IL-2 dosing regimen or multiple cycles of a multi-level IL-2 dosing regimen is at the discretion of the managing physician and can be assessed by monitoring Treg cells in subjects undergoing treatment with the method of the invention.

In a preferred embodiment, in a patient with autoimmune disease, it is best to reach and/or maintain the Tregs percent level between 5-10% total T cells.

In a preventive setting, it is desirable to reach and/or maintain Tregs percent level between 4.5-7% total T cells.

IL-2 doses may be adapted according to patients' response, i.e. the effects on Treg percentage and their activation status (CD25).

It is thus described a method for determining whether a IL-2 regimen or dose has to be modified in a patient with an autoimmune, an immune-related or an inflammatory disorder, treated with IL-2, which method comprises monitoring the quantity of Tregs and/or CD25 expression level in Tregs.

A quantity of Tregs and/or CD25 expression level in Tregs inferior to the control value, means that the dose of IL-2 is to be increased. The control value is generally the baseline quantity of Tregs and/or CD25 expression level in the patient, before any treatment.

In a particular embodiment, such quantification can be conducted when the treatment is initiated (e.g. between 3 to 5 days after the first administration). If Tregs percentages or CD25 expression levels are below a 20% increase compared to baseline, the dose of IL-2 can be increased (e.g. ×2) and the process repeated until a dose (below 3.5 MIU/day) inducing proper Treg response is found.

Preferably this method is also conducted during the maintenance period, which involves quantifying the number of Tregs and/or the expression level of CD25 in Tregs every 2 to 6 months, preferably between 1 to 5 days after administration of IL-2. If Tregs percentages or CD25 expression levels are below a 20% increase compared to baseline, the dose of IL-2 could be increased (e.g. ×2).

Administration Forms and Routes 11-2 may be administered using any acceptable method known per se in the art. Thus, for example, IL-2, or the pharmaceutical composition comprising IL-2, can be administered by any form of injection, including intravenous (IV), intramuscular (IM), or transdermal or subcutaneous (SC) injection, or by oral or nasal route as well as by topical administration (cream, droplets, etc.). In a particular embodiment of the invention, IL-2 is used as a sustained-release formulation, or a formulation that is administered using a sustained release device. Such devices are well known in the art, and include, for example, transdermal patches, and miniature implantable pumps that can provide for drug delivery over time in a continuous, steady-state fashion at a variety of doses to achieve a sustained-release effect.

Sublingual or eye drop formulations may also be contemplated.

IL-2 is typically administered in association (e.g., in solution, suspension, or admixture) with a pharmaceutically acceptable vehicle, carrier or excipient. Suitable excipients include any isotonic solution, saline solution, buffered solution, slow release formulation, etc. Liquid, lyophilized, or spray-dried compositions comprising IL-2 or variants thereof are known in the art and may be prepared as aqueous or nonaqueous solutions or suspensions.

Preferably the pharmaceutical compositions comprise appropriate stabilizing agents, buffering agents, bulking agents, or combinations thereof to minimize problems associated with loss of protein stability and biological activity during preparation and storage.

A buffering agent may be used to maintain pH of the liquid composition within an acceptable range for stability of IL-2. The buffering agent may be an acid such as e.g., succinic acid, citric acid, phosphoric acid, and glutamic acid.

Examples of suitable bulking agents include e.g., glycine, mannitol, or valine, or any combination thereof.

Examples of inert carriers which may be used as stabilizing agents include sugars (e.g., sucrose, glucose, dextrose) and sugar alcohols, as well as amino acids.

The pharmaceutical composition may additionally incorporate other stabilizing agents, such as methionine, a non-ionic surfactant such as polysorbate 80, etc.

Specific examples of IL-2 formulations are described [10] and in U.S. Pat. No. 4,604,377.

Where IL-2 is in monomeric form, it is preferred to add to the compositions an amino acid base sufficient to decrease aggregation of IL-2 during storage. The amino acid base can be an amino acid or a combination of amino acids, where any given amino acid is present either in its free base form or in its salt form. Examples of such amino acids include arginine, lysine, and aspartic acid.

In a particular embodiment, the composition comprises a multimeric IL-2, for example lyophilized.

A specific example of such a composition is Proleukin® IL-2. This lyophilized formulation comprises selectively oxidized, recombinant IL-2 admixed with a water soluble carrier, such as mannitol, that provides bulk, and SDS to ensure solubility of IL-2 in water. This composition is suitable for reconstitution in aqueous solutions for parenteral injection.

Packaging

The current packaging of IL-2 is vials containing 18 M IU of IL-2. Given the low dose to be used, packaging for dose of 0.01 M IU, 0.02 M IU, 0.5 M IU 0.1 M IU, 0.2 M IU, 0.5 M IU, 1 M IU and 3, or 3.5 M IU are preferably prepared.

A specific object of this invention therefore also resides in a pharmaceutical composition comprising a unit dose of 3 M IU IL-2, or less. The composition may be in a vial, capsule, syringe, etc.

Treatment of Autoimmune and Inflammatory Diseases

The invention may be used for the treatment of any condition associated to or caused by an undesirable immune response and/or in which a Treg quantitative or qualitative defect has been described. Examples of such diseases include autoimmune diseases, inflammatory diseases (including any human disease in which an inflammation process plays an important role), as well as immune-related diseases.

The treatment may be curative or preventive. In a particular embodiment, the treatment is curative, i.e., concerns a subject in whom the disease is declared, even at very early stages. In such patients, the treatment aims at reducing or stopping disease progression and/or suppressing disease symptoms or causes. The treatment may lead to complete disappearance of disease in the patient, as illustrated in the examples.

The treatment may be preventive, i.e., in patients not having declared a disease or in patients in remission of a disease to prevent relapses, such as in the case of multiple sclerosis. In such patients, the treatment aims at maintaining an elevated level of Tregs and/or reducing inflammation in order to avoid development of a disease caused by undesirable immune reaction.

Treatment designates any improvement in the patient condition, such as a reduced pain, a reduced tissue injury, etc.

A Treg defect has been reported in various autoimmune human diseases, and the invention is particularly suited for treating inflammatory or autoimmune diseases, including without limitation HCV-related vasculitis, uveitis, myositis, type I diabetes, systemic lupus erythematous, systemic vasculitis, psoriasis, allergy, asthma, Crohn's disease, multiple sclerosis, rheumatoid arthritis, atherosclerosis, autoimmune thyroid disease, auto-inflammatory diseases, neuro-degenerative diseases, Alzheimer disease, graft-versus-host disease, spontaneous abortion and allograft rejection. The invention may be used as an adjunct treatment for inflammatory infection-related pathologies such as Chagas disease, Leishmaniasis, *Helicobacter pylori* infection, chronic viral hepatitis (B, C, D), HIV, HTLV, Malaria, Amoebiasis, or Shigellosis, all characterized by a high degree of inflammation or conditions involving an inflammatory component affecting the therapy such as post-surgical local inflammation.

Chronic HCV infection is uniquely associated with an array of extrahepatic complications, which pathogenic mechanisms appear to be largely immunologically driven. Among these, cryoglobulinemia and its clinical sequelae hold the strongest association. Cryoglobulins are readily detectable in 40-60% of HCV-infected patients [11, 20, 21, 22] whereas overt cryoglobulinemia vasculitis (mixed cryoglobulinemia: MC) develops in only 5-10% of the cases [11]. The most frequent target organs are skin, joints, nerves and kidney. The disease expression is variable, ranging from mild clinical symptoms (purpura, arthralgia) to fulminant life-threatening complications (glomerulonephritis, widespread vasculitis). The observation of T cells in vascular infiltrates, the presence of autoantibodies and the observation that some HLA groups confer susceptibility to MC in HCV-infected patients support the autoimmune nature of this virus-linked pathology [12, 13]. MC pathophysiology appears to result from the interaction between HCV and lymphocytes, which directly modulates B- and T-cell function and results in polyclonal activation and expansion of B cell producing IgM with rheumatoid factor (RF) activity [23]. We previously reported that Tregs are significantly reduced in HCV-MC patients [12, 14, 15]. Moreover, in MC patients that could be successfully treated for HCV, virus clearance was associated vasculitis cure and Treg recovery.

The experimental section reports the results of a phase I/IIa study designed to assess the safety, immunological effects and clinical efficacy of repeated administration of low-dose IL-2 therapy in HCV-infected patients with associated autoimmunity. We show that low-dose IL-2 is well tolerated, induces a dramatic and selective increase in Treg cells, and leads to clinical improvement in all patients treated. This is the first demonstration of in vivo Treg induction and recovery after IL-2 immunotherapy in a human autoimmune disease.

As reported in the examples, the treatment was well tolerated and did not induce effector T cells activation, vasculitis flare or increased HCV viremia. Low-dose IL-2 dramatically increased the proportions of CD4+ CD25hiCD127−Foxp3+ Tregs with potent suppressive activity in all patients, and concomitantly decreased marginal zone B cells proportions. Transcriptome studies of peripheral blood mononuclear cells showed that IL-2 induced a global attenuation of inflammatory/oxidative stress mediators. Reduced cryoglobulinemia and/or clinical improvement of the vasculitis were observed in 90% (9/10) and 80% (8/10) of patients, respectively.

This is the first demonstration of Treg cell recovery and clinical improvement after a well tolerated low-dose IL-2 immunotherapy in a human autoimmune disease. It paves the way for a broader use of IL-2 for treating inflammatory and autoimmune diseases.

Other diseases include:
Systemic inflammatory response syndrome (SIRS) (choc) (adjuvant);
Liver graft—neoadjuvant and adjuvant therapy for prevention of inflammatory hepatic fibrosis—treating donor and/or recipient for improved graft control
Liver cirrhosis—for prevention of inflammatory hepatic fibrosis and related complications
Auto-inflammatory systemic diseases—reduction or prevention of inflammatory reaction with clinical/biological flares
Acute respiratory distress syndrome (ARDS) (adjuvant)
Acute pancreatitis—reduction of inflammatory reaction and secondary necrosis
Vascular surgery—stent—prevention of stent occlusion by preventing inflammatory reaction to stent insertion
Improvement of cardiac remodelling following cardiac infarction
Orthopaedic surgery—reduction of inflammatory reaction following OS
Odontology—treatment of peridontitis
Still disease
Psychiatry: Depression The following examples are given for purposes of illustration and not by way of limitation.

EXAMPLES

Example 1: Low-Dose IL-2 in HCV-Related Vasculitis

Here, we provide the first biological evidence in human subjects that IL-2 can be used under conditions that induce Tregs without inducing Teffs in patients with auto-immunity. We report here the first demonstration of in vivo expansion of very potent suppressive Treg through IL-2 immunotherapy in a human autoimmune disease, leading to clinical improvement. The primary end point of our study, increased Treg at the end of IL-2 therapy, and all secondary end points, including the clinical response were all met. We show that low-dose IL-2 is well tolerated, induces a dramatic and selective increase in Treg cells, and leads to clinical improvement in 80% of the patients. This is the first demonstration of in vivo Tregs induction and recovery after IL-2 immunotherapy in a human autoimmune disease. Furthermore, we show for the first time a marked anti-inflamatory effect of low-dose IL-2 in humans.

Methods

Patients

Inclusion criteria for the study were as follows: 1) chronic active HCV infection defined by a positive HCV RNA; 2) a history of MC vasculitis defined by the (i) presence of serum cryoglobulin ≥0.05 g/l in at least two determinations and (ii) the presence of the triad purpura-arthralgia-asthenia or (iii) biopsy proven vasculitis (kidney, nerve or skin) in the absence of purpura [16, 17]; 3) presence at inclusion of a clinically active vasculitis with resistance or intolerance to conventional therapies, i.e. antiviral therapy (Peg-Interferon-α and ribavirin) and/or Rituximab; 5) a minimum of 6 or 2 months after discontinuing Rituximab or antiviral therapy, respectively.

Exclusion criteria included co-infection with hepatitis B virus or HIV, liver cirrhosis, cancer or lymphoma, any immunosuppressant use in the last 6 months, drug addiction, alcohol abuse or pregnancy.

Study Design

We conducted a monocenter open prospective phase I/II trial. Four cycles of 5-days subcutaneous IL-2 therapy were administered. The first cure was carried out at the dose of 1.5 millions IU/day during a one week hospitalization to evaluate tolerance. Based on satisfactorily tolerance, the 3 later cures were done ambulatory at the dose of 3 millions IU/day. The second cure was started after a 10-day washout, while the following 2 cures after a 17-day washout period. The study was approved by institutional ethics committee and informed consent was obtained from all patients. Patients were evaluated on day-1 and day-5 of each cure, prior to the first and last IL-2 administration of that cure. They were also evaluated 48 to 90 days after the last IL-2 administration.

The response to treatment was analysed by comparing clinical, immunologic, and virologic parameters at the initial evaluation, at the end of each course of IL-2 (at weeks 1, 3, 6 and 9) and at the end of follow-up. Clinical response was defined by analysing the progression of the following main clinical signs: skin involvement (absence of purpura and/or leg ulcer), peripheral neuropathy (clinical and electrophysiologic improvement on two successive examinations), renal involvement (normalization of serum creatinine level and disappearance of proteinuria and/or hematuria), and absence of arthralgia.

The primary end point was a 4% absolute increase of $CD4^+CD25^+Foxp3^+$ regulatory T cell (Treg) proportion at the end of IL-2 therapy (i.e. at W9). Secondary end points included safety, evaluation of cellular and humoral immunity at W9, persistent increase of Treg levels at distance from treatment (W19) and evaluation of clinical response of the vasculitis.

Flow Cytometric Analysis

The immunomonitoring was performed according to previously published routine methods used in the Pitié-Salpêtrière Biotherapy department.

Briefly, peripheral blood mononuclear cell (PBMC) subsets ($CD3^+$, $CD4^+$, $CD8^+$ T lymphocytes, $CD19^+$ B lymphocytes and $CD3^-CD56^+$ NK cell) counts (cells/µl) were established from fresh blood samples using CYTO-STAT tetraCHROME kits with Flowcount fluorescents beads as internal standard and tetra CXP software with a FC500 cytometer according to manufacturer's instructions (Beckman Coulter, Villepinte, France). Subsets of these cells were analysed using multicolour flow cytometry and mAbs directly conjugated to various fluorescent markers. Cells acquisition and analysis by flow cytometry were performed using a FC500 Cytometer (Beckman Coulter). Instrument setting parameters (gains, compensations, and threshold) were set with machine software (CXP Software; Beckman Coulter) in conjunction with calibration beads (Flow-set beads, Cytocomp kit, and CYTO-TROL Control Cells). Machine reproducibility was verified with standardized beads (Flow-check). Data were analyzed with CXP analysis software (Beckman Coulter).

Subsets of these cells were analysed using multicolour flow cytometry and mAbs directly conjugated either to Fluorescein isothiocyanate (FITC), Phycoerythrin (PE), Phycoerythrin-Texas Red (ECD), Allophycocyanin (APC) or phycoerythrin-Cyanyn 7 (PE-Cya7) were used for: CD3-ECD or -PC7, CD4-ECD or -PC7, CD8-PC7, CD8-APC, CD14-PE, CD16-FITC, CD19-ECD, CD28-FITC, CD45RA-APC, CD45RO-FITC, CD56-PE CD69-PE, CD152-PE and HLA-DR-PC7 all from Beckman Coulter (Villepinte, France). CD25-PE, CD25APC, CD27-PE, CD62L-FITC and IgD-FITC, were from BD Biosciences (Le Pont De Claix, France). CD127 was from e-Biosciences (San Diego, Calif., USA), and glucocorticoid-induced tumour necrosis factor-related protein (GITR)-PE from Miltenyi Biotech (Paris, France). Latency-associated peptide (LAP)-PE and CCR7-PE antibodies were from R&D Systems (Abingdon, UK). Intracellular CD152 labelling was performed using Fix and Perm reagent from Invitrogen (Cergy Pontoise, France) after CD3, CD4, CD127 and CD25 membrane staining. Matched mouse isotype control antibodies were used. Intranuclear FOXP3 labeling was performed after CD3, CD4, CD127 and CD25 membrane staining using APC anti-human Foxp3 kit (PCH101 clone, eBiosciences) according to manufacturer's instructions. Rat IGg2a APC was used as isotypic control (eBiosciences).

Cells acquisition and analysis by flow cytometry were performed using a FC500 Cytometer (Beckman Coulter). Instrument setting parameters (gains, compensations, and threshold) were set with machine software (CXP Software; Beckman Coulter) in conjunction with calibration beads (Flow-set beads, Cytocomp kit, and CYTO-TROL Control Cells). Machine reproducibility was verified with standardized beads (Flow-check). Data were analyzed with CXP analysis software and Kaluza software (Beckman Coulter) For detection of intracellular cytokine production, PBMC were stimulated with 50 ng/ml PMA and 1 mM ionomycin in the presence of Golgi-Stop (BD Biosciences) for 4 hr and then stained with anti-IFN-g-FITC (eBioscience), or anti-IL-17-Alexa Fluor 647 (e-Bioscience) after fixation and permeabilization, according to the manufacturer's instructions.

Suppression T Cell Assays

Cells suppression assay was performed as previously described. Briefly, PBMC were stained with appropriate combinations of mAbs in order to purify by flow cytometer (FACS Aria, BD Biosciences) CD3+CD4+CD25+CD127low/− cells namely FACS-sorted Treg. To test their suppressive activity, Treg were assayed in round-bottomed 96-well tissue culture plates mixed at various cell ratios (1/1; 1/2; 1/4; 1/8; 1/16) with $5 \times 10^4$ autologous Facs-sorted CD4+CD25− cells as responder cells in the presence of $10^4$ irradiated (15 grays) allogeneic PBMC as stimulator cells in 200 µL of complete culture medium. Triplicates were performed for each culture condition. After 4 days, cell proliferation was determined by incorporation of 1 µCi (0.037 MBq) of $^3$H-thymidine (Amersham, Buckinghamshire, UK) for an additional 16 h and measured using a β-counter (counter-WALLAC). Results were expressed in counts per minute (cpm) and percentage of suppression of proliferation was determined by proliferation of effector cells without treg/proliferation of effector cells with treg ratio.

Transcriptome Studies

RNAs were generated using RNeasy Mini Kit (QIAGEN, requis, CA) according to the manufacturer's instructions. RNA integrity was assessed using an Agilent Bioanalyser showing a quality of RNA integrity number of 7-9.5 (Agilent Technologies). RNA yield was assessed using a NanoDrop 1000 spectrophotometer (NanoDrop Products, Thermo Fisher Scientific). Total RNA was amplified and converted to biotinylated cRNA according to the manufacturer's protocol (Illumina TotalPrep RNA Amplification Kit; Ambion).

Labelled cRNA were hybridized overnight to Illumina Human HT-12 V3 BeadChip arrays (Illumina), which contained more than 48,000 probes. The arrays were then washed, blocked, stained and scanned on an Illumina Bead-Station following the manufacturer's protocols. Illumina BeadStudio software (Illumina) was used to generate signal intensity values from the scans. Data were normalized according to the quantiles method and supervised hierarchical clustering was performed on 435 selected transcripts that were significantly modulated after treatment in at least 3 out of 6 patients. Modulation threshold ratios were set up at 0.6 and 1.5 for down and up-regulated transcripts respectively. One patient presenting too divergent modulation profiles from the others was excluded from the clustering analysis. Gene signatures were analyzed to generate functional networks using the PredictSearch™ software (Prediguard), a datamining bioinformatic solution dedicated to identify relevant correlations between genes and concepts, was used to generate functional networks. This tool is daily updated with the whole NCBI Pubmed database and seeks for relevant correlations between gene-gene or gene-concept within abstracts cocitations.

Correlations are also retrieved from the crosscomparison to the whole set (>18000) of transcriptional signatures deposited in NCBI GEO database and extracted with the DBF-MCL algorithm using TranscriptomeBrowser tool. Furthermore PredictSearch™ allows the annotation of modulated genes according to KEGG and Biocarta pathways as well as to GO ontology.

For unsupervised analyses, potential molecular signatures were extracted using unsupervised Independent Component Analysis (ICA). Those signatures were added to the Gene Set Enrichment Analysis (GSEA) signature database and tested for their significance on our microarray data using GSEA software. GSEA leading edges of statistically significant molecular signatures (FDR q.value<0.05) were annotated for their GO terms and KEGG pathways enrichment. Signatures with enrichment for GO terms related to inflammation, immune response and autoimmune pathologies were selected. A Khi2 test was used to determine whether these selected signatures were preferentially up- or down-regulated in IL-2-treated samples as compared to the overall distribution of up- or down-regulated signatures.

Statistical Analyses

A sample size of 10 patients achieves 94% power to detect a mean of paired differences of 4% with an estimated standard deviation of differences of 3% and with a significance level (alpha) of 0.05 using a two-sided Wilcoxon signed rank test, assuming that the actual distribution of the percentage of CD4$^+$CD25$^+$Foxp3$^+$ regulatory T cell is normal.

Comparisons of baseline with W9 or Post-IL-2 measures were done with the Wilcoxon signed rank test. The F approximation of the Friedman test was used to compare across all repeated measurements [24]. Approximations of the critical region of the Friedman statistic and multiple comparisons were performed where appropriate [25].

Time-to-peak values (Tmax) were determined directly from the experimental data as the time of maximum Treg percentage (Emax).

Results

Patients

Ten patients were included (Table-1). At inclusion, the median (Q1-Q3) age was 58.5 (49.5-66.2) years with a 50/50% male to female ratio. Clinical manifestations of MC vasculitis included peripheral neuropathy (n=8), purpura (n=8), asthenia (n=6), arthralgia (n=3) and kidney involvement (n=1) [daily proteinuria 1.5 g, microscopic hematuria and creatinemia 74 μmol/L]. The median (Q1-Q3) cryoglobulin level was 0.53 (0.26-2.77) g/L, of type II IgM Kappa in all cases. The median (Q1-Q3) C4 complement factor level was 0.065 (0.02-0.16) mg/L, rheumatoid factor activity was present in 90% of cases and antinuclear antibodies were positive in one patient (at a 1/640 titer). The median HCV viral load was 6.25 (5.5-6.8) Log copies/mL; no patients had liver cirrhosis.

Safety of Low Dose IL-2

Compliance to treatment was good and all patients completed all 4 courses of IL-2. IL-2 was clinically and biologically well tolerated (Table-1). No significant changes in granulocytes, red blood cells, or liver enzymes were observed throughout the study. Only minor clinical grade 1 side effects were noted and spontaneously resolutive, including asthenia (n=4), transient local reactions at injection sites (n=4), flu-like syndrome (n=4), myalgia (n=1) and hypertension (n=1). Notably, none of these occurred at the lowest, 1.5 million IU/day, IL-2 dosage (Table-1). During the entire treatment and follow-up, there were no biological or clinical signs indicating activation of pathogenic T cells: no vasculitis flare was noted; lymphoid organ examination did not show abnormality suggestive of lymphoproliferative disorder induction; no increase in HCV viral load was observed (Table-1 & FIG. 1A).

Biological and Clinical Efficacy of Low Dose IL-2 on HCV-MC

The HCV viral load continuously decreased during the IL-2 treatment period and was significantly lower at W9 (p=0.02), in the absence of any antiviral treatment. Cryoglobulin serum levels, which also continuously decreased (P=0.014, at W9), were already decreased (P=0.003) while C4 inversely increased (P=0.027) after the first 1.5 m IU IL-2 course (FIG. 1). No patient developed antinuclear antibodies over IL-2 therapy and antinuclear antibodies disappeared in patient #1. In agreement with the improved biological parameters of HCV-MC vasculitis (FIG. 1), 8 out of 10 patients showed marked clinical improvement following IL-2 therapy, with disappearance of purpura and arthralgia (8/8 and 3/3 patients, respectively). Kidney parameters normalized (daily proteinuria <0.3 g and absence of hematuria) in patient #10. The only patients who did not have a marked clinical response were those who presented with only a neuropathy at the time of inclusion (n=2).

Low Dose IL-2 Induces a Dramatic Increase of CD4$^+$ and CD8$^+$ Regulatory T Cells IL-2 induced a dramatic increase in circulating CD4$^+$CD25$^{hi}$CD127$^-$Foxp3$^+$ Tregs (FIG. 2A and FIG. 3). The baseline percentage of Tregs in this group of patients was of 3.6%±0.23 (mean+/−sem), significantly lower than normal values (4.6±0.6) in agreement with our previously reported studies. At W9, Treg proportions were of 11.8%±1.96 (P=0.004), reaching our primary efficacy criteria endpoint. Noteworthy, Treg proportions were already increased approximately 2-fold after the first 5-day course of 1.5 million IU of IL-2 (FIG. 2A). Treg proportions continued to increase during the wash-out period between courses, and were further boosted by the subsequent courses (FIG. 2A). Compared to baseline values, these increased Treg proportions were statistically significant throughout treatment (P=0.016 at W1 and P<0.001 at W3, 6 and 9). The median peak value of Tregs proportion (Emax=14%) was reached at the end of the third IL-2 course (median Temax=2.9), corresponding to an increase of 10.3% compared to baseline (Emax minus Baseline) or corresponding to a 350% increase of Tregs (Emax/Baseline). At distance (129 to 150 days) from the treatment, Treg proportion remained significantly elevated, at twice the baseline value (6.1%±0.51, P=0.008), in the range of values for normal blood donors. Finally, we evaluated the functionality of the IL-2 expanded Tregs and found that they were highly suppressive (FIG. 4).

A population of rare CD8$^+$CD25$^{hi}$Foxp3$^+$ T cells with suppressor function can be detected in normal individuals [26] (FIG. 5). We monitored these cells during the IL-2 treatment and observed their marked increase, concomitant to the CD4$^+$ Treg increase. Following the first course their proportion increased by approximately 500% and it remained elevated throughout treatment (FIG. 2A, Table-2). Altogether, the increase of CD4$^+$ and CD8$^+$ Tregs leads to a striking increase in the global Treg/Teff ratio, with no modification of the CD4/CD8 ratio (FIG. 2B, Table-2).

Total B cell numbers decreased during IL-2 treatment, immediately after the first course, and then recovered at distance from therapy. This decrease particularly affected the IgD$^+$CD27$^+$ marginal zone B cells that are implicated in the vasculitis pathophysiology [27] (FIG. 2C, FIG. 6). In contrast, there was a significant increase in numbers of NK cells, which was already detected following the first IL-2 course, and showed a clear tendency to continuous increase over time; this rapidly ceased after IL-2 discontinuation. There was notably a specific increase of the $CD56^{bright}$ NK cells that produce high levels of immunoregulatory cytokines and are poorly cytotoxic (FIG. 2D, Table-2).

Low Dose IL-2 Induces a Global Decrease of Inflammation Revealed by Transcriptome Analyses of PBMCs We analysed the transcriptome of PBMCs before and after IL-2 course (FIG. 3. We first performed a supervised analysis, comparing directly the two sets of data and looking for genes that are up- or down-regulated between the two conditions. This study first confirmed the phenotypic observations, showing increased expression of genes related to Treg and NK cell function, together with a decreased expression of genes related to B cell function (not shown). Hierarchical clustering and data mining approaches revealed a striking decrease in the expression of genes associated with inflammatory/oxidative stress mediators (FIG. 7A). The NFKB pathway appears crucially involved in this regulation (FIG. 7B). We confirmed these results by an unsupervised (i.e. non hypothesis driven) analysis. In this approach, all the pre- and post-IL-2 transcriptome data are mixed together, and signatures maximizing the segregation of the data in independent groups are sought based on Independent Component Analysis (ICA) [28]. Gene Ontology (GO) terms and pathways (GOTP) are then looked for among the signatures that differentiated pre- and post-treated groups. The ratio of up- versus down-regulated GOTP was of 0/251 for Inflammation ($p=1.3E-40$), 16/684 for Immune responses ($p=3.4E-94$) and 77/555 for Lymphocyte Activation ($p=7.0E-49$) (FIG. 3C). Conversely, we obtained 1701 up- and 208 down-regulated signatures enriched with the GOTP related to Cell Cycle ($p=1.5E-138$). Similar analysis with randomly chosen control terms showed no enrichment.

A similar analysis was then performed on Kyoto Encyclopedia of Genes and Genomes (KEGG) pathways terms related to autoimmune, inflammatory, and transplantation-related pathologies and infectious diseases. These signatures were preferentially down-regulated after IL-2 treatment ($p=7.6E-09$ and $p=7.6E-36$, respectively), while control pathologies were not.

TABLE 1

Characteristics and outcome of HCV related autoimmune vasculitis patient under IL-2 therapy

| Characteristics | Patient 1 | Patient2 | Patient 3 | Patient 4 | Patient 5 | Patient 6 | Patient 7 | Patient 8 | Patient 9 | Patient 10 |
|---|---|---|---|---|---|---|---|---|---|---|
| Age at diagnosis (years) | 48 | 74 | 63 | 50 | 59 | 67 | 51 | 66 | 58 | 43 |
| Gender | female | female | male | male | male | male | female | male | female | female |
| Symptoms | | | | | | | | | | |
| Baseline | P, A, F | P, N, F | P, N, F | N, F | P, N, F | P, N | P, N | N | A, P | A, P, N, K, F |
| Post IL-2 therapy | — | — | N | N | — | — | — | N | — | N |
| Previous therapy | Peg IFN/ RBV | Peg IFN/ RBV | Peg IFN/ RBV | Peg IFN/ RBV | Peg IFN/ RBV | Peg IFN/ RBV | Peg IFN/ RBV | Peg IFN/ RBV | Peg IFN/ RBV | Peg IFN/ RBV |
| | | Rituxan | | | | | | | | Rituxan |
| Cryoglobulin serum level (g/L) | | | | | | | | | | |
| Baseline | 0.56 | 1.61 | 0.17 | 0.16 | 0.30 | 0.3 | 6.99 | 2.77 | 2.78 | 0.51 |
| Post IL-2 therapy | 0 | 1.00 | 0.91 | 0 | 0.34 | 0 | 3.87 | 1.99 | 2.94 | 0.19 |
| C4 complement level (g/L) | | | | | | | | | | |
| Baseline | 0.20 | 0.06 | 0.08 | 0.20 | 0.06 | 0.15 | 0.07 | 0.02 | 0.03 | 0.02 |
| Post IL-2 therapy | 0.21 | 0.05 | 0.12 | 0.27 | 0.09 | 0.19 | 0.10 | 0.06 | 0.04 | 0.03 |
| HCV viral load (Log UI/mL) | | | | | | | | | | |
| Baseline | 5.3 | 6.2 | 7.2 | 6.3 | 5.6 | 6.9 | 5.8 | 6.3 | 6.8 | 5.4 |
| Post IL-2 therapy | 5.2 | 5.8 | 5.6 | 6.2 | 5.6 | 5.8 | 6.0 | 5.1 | 4.6 | 5.5 |
| Alanine aminotransferase (IU/L) | | | | | | | | | | |
| Baseline | 26 | 38 | 29 | 25 | 77 | 40 | 58 | 60 | 104 | 40 |
| Post IL-2 therapy | 19 | 17 | 45 | 24 | 81 | 23 | 22 | 62 | 80 | 35 |
| IL-2 therapy Side effects | | | | | | | | | | |
| Course 1 (1.5 M U/day for 5 days) | — | — | — | — | — | — | — | — | — | — |
| Course 2 (3 M U/day for 5 days) | — | F, M | F | F | F | Flu, LR | Flu, LR | Flu, LR | AH | Flu, LR |
| Course 3 (3 M U/day for 5 days) | — | F | F | F | F | LR | Flu | Flu, LR | AH | — |
| Course 4 (3 M U/day for 5 days) | — | — | — | — | — | LR | — | LR | — | — |

A: arthralgia,
F: fatigue,
P: purpura,
N: neuropathy,
K: kidney involvement,
M: myalgia,
Flu: Flu-like syndrom,
LR: local reaction,
AH: arterial hypertension

TABLE 2

Immunologic characteristics under IL-2 therapy

| | Baseline | End of Course 1 | End of Course 2 | End of Course 3 | End of Course 4 | Post IL-2 |
|---|---|---|---|---|---|---|
| Lymphocytes (cells/μl) | 685 (242-2008) | 838 (267-1817) | 746 (238-1529) | 781 (398-2320) | 855 (558-1859) | 871 (426-2302) |
| T cells (cells/μl) | 633 (242-1214) | 655 (401-1214) | 456* (284-1334) | 506 (250-1237) | 647 (292-1660) | 690 (299-936) |
| Total CD4 T cells (cells/μl) | 298 (149-1193) | 456 (118-1009) | 335 (91-658) | 403 (94-1192) | 340 (173-1041) | 531 (151-984) |
| Total CD8 T cells (cells/μl) | 234 (73-681) | 191 (36-531) | 130* (64-414) | 147* (77-680) | 223 (104-448) | 292 (84-518) |
| CD4/CD8 ratio | 1.9 (1.4-4.3) | 1.8 (1-5.3) | 1.6 (1.1-5.2) | 1.7 (0.9-5.1) | 1.96 (0.8-4.9) | 1.8 (1.3-4.9) |
| NK cells (cells/μl) | 63 (49-184) | 97* (44-245) | 155** (13-290) | 164** (50-269) | 209*** (79-389) | 77 (41-229) |
| CD56 bright NK cells (cells/μl) | 8 (5-17) | 18** (8-30) | 27*** (2-100) | 20** (6-58) | 27*** (8-93) | 7*** (2-12) |
| B cells (cells/μl) | 118 (18-570) | 90 (20-334) | 84* (27-236) | 86* (24-342) | 98 (29-175) | 111 (30-522) |
| MZ B cells (cells/μl) | 12 (1-77) | 4* (1-35) | 3* (1-14) | 3** (1-15) | 4** (1-14) | 3 (1-42) |
| Treg | | | | | | |
| CD4+ CD25hiCD127-Foxp3+ (cells/μl) | 15 (5-29) | 25 (8-71) | 29*** (9-92) | 31** (14-221) | 36** (20-271) | 31** (12-62) |
| % CD25hiCD127-FoxP3+/CD4+ | 3.8 (1.8-4.4) | 6.8* (3.7-15) | 10.4*** (5-24) | 10*** (3.2-29) | 11*** (6-26) | 6** (3-8) |
| CD8+ Foxp3+ (cells/μl) | 0.08 (0.03-1.36) | 0.46* (0.03-3.71) | 0.46* (0.11-3.31) | 0.62** (0.12-6.8) | 0.47** (0.17-2.68) | 0.19 (0.07-0.64) |
| % CD25+ FoxP3+/CD8+ | 0.04 (0.01-0.2) | 0.35*** (0.02-0.7) | 0.24*** (0.08-0.99) | 0.2*** (0.11-1) | 0.28*** (0.08-0.6) | 0.08 (0.03-0.24) |
| % Treg/Teff (CD4+ CD8) | 4 (2-6) | 9.5** (4-17) | 13*** (9-53) | 14.5*** (6-42) | 14*** (7-32) | 6** (4-13) |
| CD4+ T cells | | | | | | |
| % CD25+ (without Treg) | 44 (20-59) | 29 (10-63) | 16*** (5-32) | 23*** (10-40) | 28** (7-48) | 46 (17-66) |

Results shown are median with range in parentheses for each cell populations analysed for the 10 patients included in the protocol.
Statistical analysis was done by Wilcoxon ranked-sum test;
*$P < 0.05$;
**$P < 0.01$;
***$P < 0.001$ versus baseline

Example 2: Low-Dose IL-2 in Type 1 Diabetes

The inventors initiated an IL-2 dose-finding clinical trial in T1D, which aimed to define the lowest active dose that could safely induce Tregs in adult T1D patients.

The DF-IL2 trial is double blinded, comparing placebo, 0.3, 1 and 3 mIU/day Proleukin® doses (cumulative dose of 1.5, 5 and 15 mIU, respectively).

The objective of the trial will be to preserve remaining endogenous insulin secretion in patients with recently diagnosed T1D.

Main patient characteristics: adults, both sexes, T1D diagnosis as WHO-ADA, disease duration since diagnosis of less than 12 weeks at first IL-2 dosing and detectable C-peptide at entry.

The current recommendation for a clinically meaningful effect is to target with the active treatment at least a preservation of pancreatic β-cell mass, i.e. the maintenance of C-peptide AUC0-120 compared to baseline.

All 24 patients have been included. Although the investigators are still blind to the IL-2 dose administered, the results obtained so far show that IL-2 is safe (no SAE in any of the patients). Minor adverse events (mild fever, moderate pain at the injection site . . . ) have been observed in some patients and based on safety data from our previous clinical trial 40 are most likely related to the dose of 3 mIU/day. An interim analysis of the Treg dynamic for the first 16 patients who have completed their treatment has been performed by an independent statistician and without un-blinding the study to the investigators (following authorisation from regulatory authorities). This interim study shows that (i) IL-2 can indeed induce Tregs in T1D patients and (ii) the dose of 1 mIU per day induces a good Treg response that last over 2 weeks (see FIG. 8).

Importantly, it was not detected in patients significant decrease of C-peptide production. C-peptide measurement after a MMTT (mixed-meal tolerance test) shows at least preserved or sometimes increased C-peptide production 2 months after the 5-day IL-2 treatment in patients, as shown for patient 1 on FIG. 9B (note that we do not know the dose received by this patient, but that the increase in Treg observed during treatment indicates that he received IL-2, not the placebo).

Following this first study with adult T1D patients, the inventors conceived a second dose finding trial, for childhood T1D, with inclusion of patients from >7 years old (DF-IL2-child). We refined our dose finding study based on our results in the above-described trial. A dose range of 0.125 to 1 mUI/m2/d (here defined as ultra-low dose) is being investigated over a one-year treatment period (16 injections), with the aim to confirm tolerance and efficacy for Treg induction. This corresponds to a cumulative dose of 2 to 16 mUI/m2, more than 100 times less than in the above described study.

Collectively, our clinical results relieve the concern that IL-2 might not be as effective in Treg induction in T1D patients who have alterations of the IL-2/IL-2R activation pathway. They also confirm the excellent tolerance of IL-2 at the doses used and support that 0.5 mUI/m2/day is an appropriate dose for assessing IL-2 efficacy in recently diagnosed TID patients, children and adults.

REFERENCES

1. Gillis S et K A Smith. Long term culture of tumour-specific cytotoxic T cells. Nature 1977; 268: 154-6.
2. Gillis S et J Watson. Biochemical and biological characterization of lymphocyte regulatory molecules. V. Identification of an interleukin 2-producing human leukemia T cell line. J Exp Med 1980; 152: 1709-19.
3. Ahmadzadeh M et S A Rosenberg. LL-2 administration increases CD4+CD25(hi) Foxp3+ regulatory T cells in cancer patients. Blood 2006; 107: 2409-14.
4. Zhang H, K S Chua, M Guimond, V Kapoor, M V Brown, T A Fleisher, et al. Lymphopenia and interleukin-2 therapy alter homeostasis of CD4+CD25+ regulatory T cells. Nat Med 2005; 11: 1238-43.
5. Papiernik M, M L de Moraes, C Pontoux, F Vasseur et C Penit. Regulatory CD4 T cells: expression of IL-2R alpha chain, resistance to clonal deletion and IL-2 dependency. Int Immunol 1998; 10: 371-8.
6. Malek T R. The biology of interleukin-2. Annu Rev Immunol 2008; 26: 453-79.
7. Williams M A, A J Tyznik et M J Bevan. Interleukin-2 signals during priming are required for secondary expansion of CD8+ memory T cells. Nature 2006; 441: 890-3.
8. Grinberg-Bleyer Y, A Baeyens, S You, R Elhage, G Fourcade, S Gregoire, et al. IL-2 reverses established type 1 diabetes in NOD mice by a local effect on pancreatic regulatory T cells. J Exp Med; 207: 1871-8.
9. Taniguchi T, Matsui H, Fujita T, Takaoka C, Kashima N, Yoshimoto R, Hamuro J. Structure and expression of a cloned cDNA for human interleukin-2. Nature. 1983; 302:305-10.
10. Whittington and Faulds Interleukin-2. A review of its pharmacological properties and therapeutic use in patients with cancer Drugs (1993) 46 (3): 446-514,
11. Cacoub P, Poynard T, Ghillani P, et al. Extrahepatic manifestations of chronic hepatitis C. Arthritis Rheum 1999; 42:2204-12
12. Boyer O, Saadoun D, Abriol J, et al. CD4+CD25+ regulatory T-cell deficiency in patients with hepatitis C-mixed cryoglobulinemia vasculitis. Blood 2004; 103: 3428-30.
13. Lenzi M, Frisoni M, Mantovani V, et al. Haplotype HLA-B8-DR3 confers susceptibility to hepatitis C virus-related mixed cryoglobulinemia. Blood 1998; 91: 2062-6.
14. Saadoun D, Rosenzwajg M, Landau D, Piette J C, Klatzmann D, Cacoub P. Restoration of peripheral immune homeostasis after rituximab in mixed cryoglobulinemia vasculitis. Blood 2008; 111:5334-41.
15. Landau D A, Rosenzwajg M, Saadoun D, Trdbeden-Negre H, Klatzmann D, Cacoub P. Correlation of clinical and virologic responses to antiviral treatment and regulatory T cell evolution in patients with hepatitis C virus-induced mixed cryoglobulinemia vasculitis. Arthritis Rheum 2008; 58:2897-907.
16. Gorevic P D, Kassab H J, Levo Y, et al. Mixed cryoglobulinemia: clinical aspects and long-term follow-up of 40 patients. Am J Med 1980; 69:287-308.
17. Saadoun D, Resche Rigon M, Sene D, et al. Rituximab plus Peg-interferon-alpha/ribavirin compared with Peg-interferonalpha/ribavirin in hepatitis C-related mixed cryoglobulinemia. Blood 2010; 116:326-34.
18. Dubois & Dubois Arch Intern Med 1916, 17:863
19. Mosteller R D. "Simplified calculation of body-surface area". N Engl J Med 1987; 317:1098.
20. Nagasaka et al, Cryoglobulinemia in Japanese patients with chronic hepatitis C virus infection: host genetic and virological study. J Med Virol 2001; 65:52-7
21. Lunel et al, Cryoglobulinemia in chronic liver disease: role of hepatitis C virus and liver damage. Gastroenterology 1994:106:1291-300.
22. Donada et al, Systemic manifestation and liver disease in patients with chronic hepatitis C and type II or III mixed cryoglobulinemia. Blood 1998; 91:2062-6.
23. Agnello et al, A role for hepatitis C virus infection in type II cryoglobulinemia. N Engl J Med 1992; 327:1490-5.
24. Iman et al. Approximations of the Critical Region of the Friedman Statistic. Communications in Statistics Part a-Theory and Methods 1980; 9:571-95.
25. Conover et al. Practical non parametric statistics. John Wiley & Sons ed. New york; 1980.
26. Chaput et al, Identification of CD8+CD20+Foxp3+ suppressive T cells in colorectal cancer tissue. Gut 2009; 58: 520-9.
27. Charles et al, Clonal expansion of immunoglobulin M+CD27+ B cells in HCV-associated mixes cryoglobulinemia. Blood 2008; 111:1344-56.
28. Concannon et al, Genetics of type 1A diabetes. N Engl J Med 2009; 360:1646-54.

The invention claimed is:

1. A method for stimulating regulatory T lymphocytes (Treg) in a human patient, the method comprising administering an interleukin-2 (IL2) to a human patient in need thereof at a dose of between 0.1 and 3.5 MIU/day in a first course of treatment, which comprises administration of the IL-2 once per day for at least three consecutive days, wherein the first course of treatment increases Treg cells in the subject; and wherein the first course of treatment is followed by a maintenance dose of the IL-2, and wherein the maintenance dose is given to the human patient once every week to every four weeks.

2. The method of claim 1, wherein the dose of IL-2 in the first course of treatment is between 1.5 to 3 MIU/day.

3. The method of claim 2, wherein the dose of IL-2 in the first course of treatment is 2 MIU/day.

4. The method of claim 1, wherein the first course of treatment comprises administration of the IL-2 to the human patient for 3 to 7 days.

5. The method of claim 4, wherein the first course of treatment comprises administration of IL-2 to the human patient for 4 to 5 days.

6. The method of claim 1, wherein the first course of treatment is reproduced at multiple time periods.

7. The method of claim 6, wherein every two consecutive time periods in the multiple time periods are interrupted by a period with no treatment.

8. The method of claim 1, wherein the maintenance dose starts 1 to 4 weeks after the last dose of the first course of treatment.

9. The method of claim 1, wherein the maintenance dose is the same as the dose in the first course of treatment.

10. The method of claim 1, wherein the first course of treatment increases the ratio of Tregs to effector T (Teff) cells by at least 20%.

11. The method of claim 1, further comprising assessing increase of Treg cells in the human patient.

12. The method of claim 11, wherein the assessing step is performed by measuring the level of Treg cells in the human patient.

13. The method of claim 11, wherein the assessing step is performed by measuring the ratio between Treg cells and Teff cells.

14. The method of claim 1, wherein the human patient has a neurodegenerative disease.

15. The method of claim 1, wherein the IL-2 is a human IL-2.

16. The method of claim 1, wherein the IL-2 is aldesleukin.

* * * * *